(12) United States Patent
Siler-Khodr

(10) Patent No.: US 6,323,179 B1
(45) Date of Patent: Nov. 27, 2001

(54) CHICKEN GNRH ANALOGS AND USES THEREOF IN REGULATION OF FERTILITY AND PREGNANCY

(76) Inventor: Theresa Siler-Khodr, 13 Mayborough La., San Antonio, TX (US) 78257

( * ) Notice: Subject to any disclaimer, the term of this patent is extended or adjusted under 35 U.S.C. 154(b) by 0 days.

(21) Appl. No.: 09/419,161

(22) Filed: Oct. 15, 1999

(51) Int. Cl.$^7$ .......................... A61K 38/22; A61K 38/24; C07K 14/575; C07K 14/59
(52) U.S. Cl. ................. 514/15; 514/2; 530/313; 530/328; 530/332; 530/333; 530/335; 930/21; 930/130
(58) Field of Search .................................. 530/313, 328, 530/332, 333, 335; 514/2, 15; 930/21, 130

(56) References Cited

U.S. PATENT DOCUMENTS

| | | |
|---|---|---|
| 4,338,305 | 7/1982 | Corbin . |
| 4,945,055 | 7/1990 | Kuehl . |
| 5,168,061 | 12/1992 | Siler-Khodr . |

OTHER PUBLICATIONS

Burgus R, Guillemin R 1970 Hypothalamic releasing factors. Ann Rev Biochem 39:499–526.

Baba Y, Matsuo H, Schally AV 1971 Structure of the porcine LH– and FSH–releasing hormone. II Confirmation of the proposed structure by conventional sequential analyses. Biochem Biophys Res Commun 44:459–463.

Gibbons JM, Mitnick M, Chieffo V 1975 In vitro biosynthesis, of TSH– and LH–releasing factors by the human placenta. Am J Obstet Gynecol 121:127–131.

Siler–Khodr TM, Khodr GS 1978 Content of Luteinizing hormone releasing factor in the human placenta. Am J Obstet Gynecol 130:216–219.

Khodr GS, Siler–Khodr TM 1978 Localization of luteinizing hormone releasing factor (LRF) in the human placenta. Fert Steril 29:523–526.

Siler–Khodr TM, Khodr GS 1979 Extrahypothalamic luteinizing hormone releasing factor (LRF): Release of immunoreactive LRF by the human placenta in vitro. Fert Steril 22:294–296.

Khodr GS, Siler–Khodr TM 1980 Placental LRF and its synthesis. Science 207:315–317.

Siler–Khodr TM, Khodr GS, Valenzuela G 1984 Immunoreactive gonadotropin–releasing hormone level in maternal circulation throughout pregnancy. Am J Obstet Gynecol 150:376–379.

Sorem KA, Smikle CB, Spencer DK, Yoder BA, Grayson MA, Siler–Khodr TM 1996 Circulating maternal CRH and GnRH in normal and abnormal pregnancies. Am J Obstet Gynecol 175:912–916.

Khodr GS, Siler–Khodr TM 1979 The effect of luteinizing hormone releasing factor (LRF) on hCG secretion. Fert Steril 30:301–304.

Siler–Khodr TM, Khodr GS 1981 Dose response analysis of GnRH stimulation of hCG releases from human term placenta. Biol Reprod 25:353–358.

Siler–Khodr TM, Khodr GS, Vickery BH, Nestor JJ, Jr. 1983 Inhibition of hCG, alpha hCG and progesterone release from human placental tissue in vitro by a GnRH antagonist. Life Sci 32:2741–2745.

Siler–Khodr TM, Khodr GS, Valenzuela G, Rhode J 1986 Gonadotropin–releasing hormone effects on placental hormones during gestation: 1. Alpha–human chorionic gonadotropin, human chorionic gonadotropin and human_chorionic somatomammotropin. Biol Reprod 34:245–254.

Siler–Khodr TM, Khodr GS, Rhode J, Vickery BH, Nestor JJ, Jr. 1987 Gestational age related inhibition of placental hCG, hCG and steroid hormone release in vitro by a GnRH antagonist. Placenta 8:1–14.

Siler–Khodr TM, IQodr GS, Valenzuela G, Harper MJ, Rhode J 1986 GnRH effects on placental hormones during gestation. 111. Prostaglandin E, prostaglandin F, and 13, 14–dihydro–15–keto–prostaglandin F. Biol Reprod 35:312–319.

Kang IS, Koong MY, Forman JS, Siler–Khodr TM 1991 Dose–related action of GnRH on basal prostanoid production from the human term placenta. The 38th Annual Meeting of the Society for Gynecologic Investigation (San Antonio) Abstract #310:253 (Abstr.).

(List continued on next page.)

*Primary Examiner*—Christine J. Saoud
*Assistant Examiner*—Olga N. Chernyshev
(74) *Attorney, Agent, or Firm*—Gunn, Lee & Keeling; Michelle Evans

(57) ABSTRACT

Specially designed non-mammalian GnRH analog decapeptides resistant to degradation by the placental enzyme, C-ase-1, or a post-proline peptidase, are disclosed. The GnRH analogs are further defined as analogs of Chicken II GnRH or Salmon GnRH. These non-mammalian analogs incorporate D-arginine, D-leucine, D-tBu-Serine or D-Trp at position 6 and ethylamide or aza-Gly-amide at position 10. The D-Arg (6)-Chicken II GnRH-ethylamide, D-Arg (6)-Chicken II GnRH-aza-Gly (10)-amide, the D-Arg (6)-Salmon GnRH ethylamide, and D-Arg (6)-Salmon GnRH-aza-Gly (10)-amide analogs are also provided, and demonstrate preferential binding to chorionic GnRH receptor that is greater relative to the biding of these analogs to pituitary GnRH receptor. These non-mammalian GnRH analogs may be used in pharmaceutical preparation, and specifically in various treatment methods as a contraceptive or post-coital contraceptive agent. The non-mammalian GnRH analogs are also provided in pharmaceutical preparations that may be used clinically for maintaining pregnancy when used in very low doses and administered in pulsatile fashion. In another aspect, the non-mammalian GnRH analogs may be used a luteolytic agents. The aza-Gly (10) amide non-mammalian analogs are yet other embodiments of the non-mammalian GnRH analogs provided as a part of the invention.

8 Claims, 8 Drawing Sheets

OTHER PUBLICATIONS

Siler–Khodr TM, Khodr GS, Harper MH, Rhode J, Vickery BH, Nestor JJ, Jr. 1986 Differential inhibition of human placental prostaglandin release in vitro by a GnRH antagonist. Prostaglandins 31:1003–1010.

Siler–Khodr, T.M. and G.S. Khodr. 1981. The production and activity of placental releasing hormones. In Fetal Endocrinology. J. Resko and W. Montagna, editors. Academic Press, Inc. New York. 183–210.

Siler–Khodr. T.M. and G.S. Khodr. 1982. GnRH in the placenta. In Role of Peptides and Proteins in Control of Reproduction. D.S. Dhindsa and S.M. McCann, editors. Elsevier North Holland, New York. 347–363.

Siler–Khodr TM 1983 Hypothalamic–like releasing hormones of the placenta. Clin Perinatol 10:553–566.

Shi LY, Zhang ZW, Li WX 1994 Regulation of human chorionic gonadotropin secretion and messenger ribonucleic acid levels by follistatin in the NUCC–3, choriocarcinoma, cell line. Endocrinology 134:2431–2437.

Steele GL, Currie WD, Yuen BH, Jia XC, Perlas E, Leung PC 1993 Acute stimulation of human chorionic gonadotropin secretion by recombinant human activin–A in first trimester human trophoblast. Endocrinology 133:297–303.

Li W, Olofsson JI, Jeung EB, Krisinger J, Yuen BH, Leung PC 1994 Gonadotropin–releasing hormone (GnRH) and cyclic AMP positively regulate inhibit subunit messenger RNA levels in human placental cells. Life Sci 55:1717–1724.

Petraglia F, Vaughan J, Vale W 1991 Inhibin and activin modulate the release of gonadotropin–releasing hormone, human chorionic gonadotropin, and progesterone from cultured human placental cells. Proc Natl Acad Sci U S A 86:5114–5117.

Petraglia F, Sawchenko P, Lim ATW, Rivier J, Vale W 1987 Localization, secretion, and action of inhibin in human placenta. Science 237:187–189.

Shi CZ, Zhuang LZ 1993 Norepinephrine regulates human chorionic gonadotropin production by first trimester trophoblast tissue in vitro. Placenta 14:683–693.

Cemerikic B, Maulik D, Ahmed MS 1993 Opioids regulation of hCG release from trophoblast tissue is mediated by LHRH. Placenta Abstract: 9(Abstr.). vol. 268, No. 2 pp. 971–977.

Petraglia F, Vaughan J, Vale W 1990 Steroid hormones modulate the release of immunoreactive gonadotropin–releasing hormone from cultured human placental cells. J Chn Endocrinol Metab 70:1173–1178.

Haning RV, Jr., Choi L, Kiggens AJ, Kuzma DL, Summerville JW 1982 Effects of dibutyryl adenosine 3', 5'–monophosphate, luteinizing honnone–releasing hormone, and aromatase inhibtor on simultaneous outputs of progesterone 17b–estradiol, and human chorionic gonadotropin by term placental explants. J Clin Endocrinol Metb 55:213–218.

Petraglia F, Lim AT, Vale W 1987 Adenosine 3', 5–monophosphate, prostaglandins, and epinephrine stimulate the secretion of immunoreactive gonadotropin–releasing hormone from cultured human placental cells. J Clin Endocrinol Metab 65:1020–1025.

Haning RV, Jr. Choi L, Kiggens AJ, Kuzma DL 1982 Effects of prostaglandins, dibutyryl camp LHRH, estrogens, progesterone, and potassium on output of prostaglandin F2a, 13, 14–dihydro–15–keto–prostaglandin F2a, hCG, estradiol, and progesterone by placental minces. Prostaglandins 24:495–506.

Barnea EP, Feldman D, Kaplan M 1991 The effect of progesterone upon first trimester trophoblastic cell differentiation and human chorionic gonadotropin secretion. Hum Reprod 6:905–909.

Barnea ER, Kaplan M 1989 Spontaneous, gonadotropin–releasing hormone–induced, and progesterone–inhibited pulsatile secretion of human chorionic gonadotropin in the first trimester placenta in vitro. J Clin Endocrinol Metab 69:215–217.

Branchaud C, Goodyear C, Lipowski L 1983 Progesterone and estrogen production by placental monolayer cultures: Effect of dehydroepiandrosterone and luteinizing hormone–releasing hormone. J Chn Endocrinol Metab 56:761–766.

Ahmed NA, Murphy BE 1988 The effects of various hormones on human chorionic gonadotropin production 'in early and late placental explant cultures. Am J Obstet Gynecol 159:1220–1227.

Iwashita M, Watanabe M, Adachi T, Ohira A, Shinozaki Y, Takeda Y, Sakamoto S 1989 Effect of gonadal steroids on gonadotropin–releasing hormones stimulated human chorionic gonadotropin release by trophoblast cells. Placenta 10: 103–112.

Haning RV, Jr., Choi L, Kiggens AJ, Kuzma DL, Summerville JW 1982 Effects of dibutyryl cAMP, LHRH, and aromatase inhibitor on simultaneous outputs of prostaglandin F2a, and 13, 14–dihydro–15–keto–prostaglandin F2a by term placental explants. Prostaglandins 23:29–40.

Wilson E, Jawad M 1980 Luteinizing hormone–releasing hormone suppression of human placental progesterone production. Fert Steril 33:91–93.

Youngblood WW, Humni J, Kizer JS 1979 TRH–like immunoreactivity in rat pancreas and eye, bovine and sheep pineals, and human placenta: Non–identity with synthetic Pyroglu–His–Pro–NH2 (TRH). Brain Res 163: 10 1–110.

Dubois MP 1975 Immunoreactive somatostatin is present in discrete cells of the endocrine pancreas. Proc Natl Acad Sci U S A 72:1340–1343.

Adashi. E.Y. 1996. The Ovarian Follicular Apparatus. In Lippincott–Raven Publishers. E.Y. Adashi. J.A. Rock, and Z. Rosenwaks, editors. Lippincott–Raven Rublishers, Philadelphia. 17–40.

Radovick S, Wondisford FE, Nakayama Y, Yamada M, Cutler GB, Jr., Weintraub BD 1990 Isolation and characterization of the human gonadotropin–releasing hormone gene in the hypothalamus and placenta. Mol Endocrinol 4:476–480.

Adelman JP, Mason AJ, Hayflick JS, Seeburg PH 1986 Isolation of the gene and hypothalamic cDNA for the common precursor of gonadotropin–releasing hormone and prolactin release–inhibiting factor in human and rat. Proc Natl Acad Sci U S A 83:179–183.

Seeburg PH, Adelman JP 1984 Characterization of cDNA for precursor of human luteinizing hormone releasing hormone. Nature 311:666–668.

Duello TM, Tsai SJ, Van Ess PJ 1993 In situ demonstration and characterization of pro gonadotropin–releasing hormone messenger ribonucleic acid in first trimester human placentas. Endocrinology 133:2617–26233.

Kelly AC, Rodgers A, Dong KW, Barrezueta NX, Blum M, Roberts JL 1991 Gonadotropin–releasing hormone and chorionic gonadotropin gene expression in human placental development. DNA Cell Biol 10:411–421.

Dong KW, Yu KL, Roberts JL 1993 Identification of a major up-stream transcription start site for the human pro gonadotropin-releasing hormone gene used in reproductive tissues and cell lines. Mol Endocrinol 7:1654–1666.

Dong KW, Duval P, Zeng Z, Gordon K, Williams RF, Hodgen GD, Jones G, Kerdelhue B, Roberts JL 1996 Multiple transcription start sites for the GnRH gene in rhesus and cynomolgus monkeys: a non-human primate model for studying GnRH gene regulation. Mol Cell Endocrinol 117:121–130.

Dong KW, Yu KL, Chen ZG, Chen YD, Roberts JL 1997 Characterization of multiple promoters directing tissue-specific expression of the human gonadotropin-releasing hormone gene. Endocrinology 138:2754–2762.

Chandran UR, Attardi B, Friedman R, Dong KW, Roberts JL, DeFranco DB 1994 Glucocorticoid receptor-mediated repression of gonadotropin-releasing hormone promoter activity in GTI hypothalamic cell lines. Endocrinology 134:1467–1474.

Dong KW, Chen ZG, Cheng KW, Yu KL 1996 Evidence for estrogen receptor-mediated regulation of human gonadotropin-releasing hormone promoter activity in human placental cells. Mol Cell Endocrinol 117:241–246.

Joss JM, King JA, Millar RP 1994 Identification of the molecular forms of and steroid hormone response to gonadotropin-releasing hormone in the Australian lungfish, Neoceratodus forsteri. Gen Comp Endocrinol 96:392–400.

Montero M, Le Belle N, King JA, Millar RP, Dufour S 1995 Differential regulation of the two forms of gonadotropin-releasing hormone (mGnRH and chorionic GnRH-11) by sex steroids in the European female silver eel (Anguilla anguilla). Neuroendocrinology 61:525–535.

Ikeda M, Taga M, Sakakibara H, Minaguchi H, Ginsburg E, Vonderhaar BK 1996 Gene expression of gonadotropin-releasing hormone in early pregnant rat and steroid hormone exposed mouse uteri. J Endocrinol Invest 19:708–713.

Gothilf Y, Meiri I, Elizur A, Zohar Y 1997 Preovulatory changes in the levels of three gonadotropin-releasing hormone-encoding messenger ribonucleic acids (mRNAs), gonadotropin. B-subunit mRNAs plasma gonadotropin, and steroids in the female gilthead seabream, Spar-us aurata. Biol Reprod 57:1145–1154.

Kang IS, Koong MK, Forman J, Siler-Khodr TM 1991 Dose-related action of gonadotropin-releasing hormone on basal prostanoid production from the human term placenta. Am J Obstet Gynecol 165:1771–1776.

Gautron JP, Pattou E, Kordon C 1981 Occurrence of higher molecular forms of LHRH in fractionated extracts from rat hypothalamus, cortex and placenta. Mol Cell Endocrinol 24:1–15.

Gautron JP, Pattou E, Bauer K, Rotten D, Kordon C 1989 LHRH-like immunoreactivity in the human placenta is not identical to LHRH. Placenta 10: 19–35.

Nowak RA, Wiseman BS, Bahr JM 1984 Identification of a gonadotropin releasing hormone-like factor in the rabbit fetal placenta. Biol Reprod 31:67–75(Abstr.).

Sherwood NM. Lovejoy DA, Coe IR 1993 Origin of mammalian gonadotropin-releasing hormones. Endocr Rev 14:241–254.

King JA, Millar RP 1995 Evolutionary aspects of gonadotropin-releasing hormone and its receptor. Cell Mol Neurobiol 15:5–23.

Kelsall R, Coe IR, Sherwood NM 1990 Phylogeny and ontogeny of gonadotropin-releasing hormone: Comparison of guinea pig, rat, and a protochordate. Gen Comp Endocrinol 479–494.

Powell JF, Reska-Skinner SM, Prakash MO, Fischer WH, Park M, Rivier JE, Craig AG, Mackie GO, Sherwood NM 1996 Two new forms of gonadotropin-releasing hormone in a protochordate and the evolutionary implications. Proc Natl Acad Sci U S A 93:10461–10464.

Powell JF, Zohar Y, Elizur A, Park M, Fischer WH, Craig AG, Rivier JE, Lovejoy DA, Sherwood NM 1994 Three forms of gonadotropin-releasing hormone characterized from brains of one species. Proc Natl Acad Sci U S A 91:12081–12085.

Montero M, Vidal B, King JA, Tramu G, Vandesande F, Dufour S, Kali O 1994 Immunocytochemical localization of mammalian GnRH (gonadotropmi-releasing hormone) and chicken GnRH-II in the brain of the European silver eel (Anguilla anguilla L.). J Chem Neuroanat 7:227–241.

White SA, Kasten TL, Bond CT, Adelman JP, Fernald RD 1995 Tbree gonadotropin-releasing hormone genes in one organism suggest novel roles for an ancient peptide. Proc Natl Acad Sci U S A 92:8363–8367.

Powell JF, Fischer WH, Park M, Craig AG, Rivier JE, White SA, Francis RC, Fernald RD, Licht P, Warby C, et al 1995 Primary structure of solitary form of gonadotropin-releasing hormone (GnRH) in cichlid pituitary; three forms of GnRH in brain of cichhd and pumpkinseed fish. Regul Pept 57:43–53.

Zohar Y, Elizur A, Sherwood NM, Powell JF, Rivier JE, Zmora N 1995 Gonadotropin-releasing activities of the three native forms of gonadotropin-releasing hormone present in the brain of gilthead seabream, Sparus aurata. Gen Comp Endocrinol 97:289–299.

Lin XW, Peter RE 1996 Expression of salmon gonadrtropin-releasing hormone (GnRH) and chicken GnRH-II precursor messenger ribonucleic acids in the brain and ovary of goldfish. Gen Comp Endocrinol 101:282–296.

Di Fiore MM, King JA, D'Aniello B, Rastogi RK 1996 Immunoreactive mammalian and chicken-II GnR_Hs in Rana esculenta brain during development. Regul Pept 62:119–124.

Powell JR, Krueckl SL, Collins PM, Sherwood NM 1996 Molecular forms of GnRH in three model fishes: rockfish, medaka and zebrafish. J Endocrinol 150:17–23.

Iela L, Powell JFF, Sherwood NM, D'Aniello B, Rastogi RK, Bagnara JT 1996 Reproduction in the Mexican leaf frog, Pachyrnedusa dacnicolor. VI. Presence and distribution of multiple GnRH forms in the brain. Gen Comp Endocrinol 103:235–243.

Powell JF, Standen EM, Carolsfeld J, Borella MI, Gazola R', Fischer W11, Park M, Craig AG, Warby CM, Rivier JE, VAl-Sella MV, Sherwood NM 1997 Primary structure of three forms of gonadotropin-releasing hormone (GnRH) from the pacu brain. REgul Pept 68:189–195.

Dellovade TL, King JA, Millar RP, Rissman EF 1993 Presence and differential distribution of distinct forms of immunoreactive gonadotropin-releasing hormone in the musk shrew brain. Neuroendocrinology 58:166–177.

King JA, Steneveld AA, Curlewis JD, Rissman EF, Millar RP 1994 Identification of chichen GnRH H in brains of inetatherian and early-evolved eutherian species of mammals. Regul Pept 54:467–477.

Kasten TL, White SA, Norton TT, Bond CT, Adelman JP, Fernald RD 1996 Characterization of two new preproGnRH mRNAs in the tree shrew: first direct evidence for mesencephalic GnRH gene expression in a placental mammal. Gen Comp Endocrinol 104:7–19.

Jimenez–Linan M, Rubin BS, King JC 1997 Examination of guinea pig luteinizing hormone–releasing hormone gene reveals a unique decapeptide and existence of two transcripts in the brain. Endocrinology 13 8:4123–4130.

Lescheid D, Terasawa E, Abler LA, Urbanski HF, Warby CM, Millar RP, Sherwood NM 1997 A second form of gonadotropin–releasing hormone (GnRH) with characteristics of chicken GnRH–11 is present in the primate brain. Endocrinology 138:1997.

White SA, Bond CT, Francis RC, Kasten TL, Fernald RD, Adelman JP 1994 A second gene for gonadotropin–releasing hormone: cDNA and expresion pattern in the brain. Proc Natl Acad Sci U S A 91:1423–1427.

Lin XW, Peter RE 1997 Cloning and expression pattern of a second His5Trp7Tyr8Igonadotrop'm–releasing hormone (chicken GnRH–H–11) mRNA in goldfish: evidence for two distinct genes. Gen Comp Endocrinol 107:262–272.

Currie A, Fraser H, Sharpe R 1981 Human placental receptors for luteinizing hormone releasing hormone. Biochem Biophys Res Commun 99:332–338.

Belisle S, Guevin J, Bellabarba. D, Lehoux J 1994 Luteinizing hormone–releasing hormone binds to enriched human placental membranes and stimulates in vitro the synthesis of bioactive human chorionic gonadotropin. J Clin Endocrinol Metab 59:119–126.

Haour, F., M. Crumeyrolle–Arias, J. Latouche, P. LeBlanc, N. Olivier, B. Augendre–Ferrante, J.F. Heurtier, and E. Ban. 1990. GnRH receptors: pharmacology and visualization in brain, ovary and placenta. In Recent Progress on GnRH and Gonadal Peptides. P. Bouchard, F. Haour, P. Franchiniont, and B. Schatz, editors. Elsevier, Paris. 91–100.

Sealfon SC, Weinstein H, Millar RP 1997 Molecular mechanism of ligand interaction with the gonadotropin–releasing hormone receptor. Endocr Rev 18:180–205.

Karten MJ, Rivier JE 1986 Gonadotropin–releasing hormone analog design. Structure–friction studies toward the development of agonists and antagonists: Rationale and perspective. Endocr Rev 7:44–66.

Escher E, Mackiewicz Z, Lagace G, Lehoux J, Gallo–Payet N, Bellabarba D, Belisle S 1988 Human placental LHRH receptor: Agonist and antagonist labeling produces differences in the size of the non–denatured, solubilize receptor. J Recept Res 8:391–405.

Bramley TA, McPhie CA, Menzies GS 1994 Human placental gonadotropin–releasing hormone (GnRH) binding sites: 111. Changes in GnRH binding levels with stage of gestation. Placenta 15:733–745.

Lin LS, Roberts VJ, Yen SS 1997 Expression of human gonadotropin–releasing hormone receptor gene in the placenta and its functional relationship to human chorionic gonadotropin secretion. J Clin Endocrinol Metab 80:580–585.

Barnea ER, Kaplan M, Naor Z 1991 Comparative stimulatory effect of gonadotropin releasing hormone (GnRH) and GnRH agonist upon pulsatile human chorionic gonadotropin secretion in superfused placental explants: reversible inhibition by a GnRH antagonist. Hum Reprod 6:1063–1069.

Szilagyi A, Benz R, Rossmanith WG 1992 The human first–term placenta in vitro: regulation of hCG secretion by GnRH and its antagonist. Gynecol Endocrinol 6:293–300.

Currie WD, Setoyarna T, Lee PS, Bairnbridge KG, Church J, Yuen BH, Leung PC 1993 Cytosohc free Ca2+ in human syncytiotrophoblast cells increased by gonadotropin–releasing hormone. Endocrinology 133:2220–2226.

Bliattacharya S, Chaudhary J, Das C 1992 Responsiveness to gonadotropin releasing hormone of human term trophoblast cells 'in vitro: induction by estradiol. Biochein Int 28:363–371.

Siler–Khodr TWI, Kang IS, Jones MA, Harper MJK' Khodr GS, Rhode J 1989 Characterization and purification of a placental protein that inactivates GnRH, TRH and Angiotensin 11. Placenta 10:283–296.

Kang IS, Siler–Khodr TM 1992 Chonionic peptidase miactivates GnRH as a post–proline peptidase. Placenta 13:81–87.

Kang IS, Gallwitz J, Guzman V, Siler–Khodr TM 1990 Definition of the enzyme kinetics and optimal activity of chorionic peptidase– 1. The 23rd Annual Meeting of the Society for the Study of Reproduction (Vancouver) (Abstract #311):144(Abstr.).

Benuck M, Marka N 1976 Differences in the degradation of hypothalamic releasing factors by rat and human serum. Life Sci 19:1271–1276.

Millar RP, King JA, Davidson JS, Milton RC 1987 Gonadotropin–releasing hormone–diversity of fictions and clinical applications. S Afr Med J 72:748–755.

Zohar Y, Goren A, Fridkin M, Elhanati E, Koch Y 1990 Degradation of gonadotropin–releasing hormones in the gilthead seabream, Sparus aurata. 11. Cleavage of native salmon GnRH, mammalian LHRH, and their analogs in the pituitary, kidney, and liver. Gen Comp Endocrinol 79:306–319.

Siler–Khodr, T.M. 1993. Luteinizing Hormone Releasing Hormone (LHRH) and the Placenta and Fetal Membranes. In Molecular Aspects of Placental and Fetal Membrane Autocoids. G.E. Rice and S.P. Brennecke, editors. CRC Press, Inc. Ann Arbor. 339–350.

Latouche J, Curmeyrolle–Afias M, Jordan D, Kopp N, Augendre–Ferrante B, Cedard L, Haour F 1989 GnRH receptors in human granulosa cells: Anatomical localization and characterization by autoradio graphic study. Endocrinology 125:1739–1743.

Petraglia F, Genazzani AD, Aguzzoli L, Gallinelli A, de Vita D, Caruso A, Genazzani AR 1994 Pulsatile fluctuations of plasma–gonadotropin–releasing hormone and corticotropin– releasing factor levels in healthy pregnant women. Acta Ostet Gynecol Scand 73:284–289.

Seshagiri PB, Terasawa E, Hearn JP 1994 The secretion of gonadotropin–releasing hormone by per–implantation embryos of the rhesus monkey: comparison with the secretion of chorionic gonadotropin. Hum Reprod 9:1300–1307.

Siler–Khodr TA4, Khodr GS, Koong MI, Valenzuela GJ, Kang IS 1991 Abnormal circulating maternal GnRH concentrations in pregnancies having post–term pregnancy. The 38th Annual Meeting of the Society for Gynecologic investigation (San Antonio) Abstract #91:144(Abstr.).

Siler–Khodr TM. Kuehl TJ, Vickery BH 1984 Effects of a gonadotropin–releasing hormone antagonist on hormonal levels in the pregnant baboon and on fetal outcome. Fert Steril 41:448–454.

Kang IS, Kuehl TJ, Siler–Khodr TM 1989 Effect of treatment with gonadotropm–releasing hormone analogues on pregnancy outcome in the baboon. Fert Steril 52:846–853.

Gupta SK, Singh M 1985 Characteristics and bioefficacy of monoclonal antigonadotropin releasing hormone antibody. Am J Reprod Immunol Microbiol 7:104–108.

Das C, Gupta SK, Talwar GP 1985 Pregnancy interfering action of LHRH and anti–LHRH. J Steroid Biochem 23:803–806.

Hodges JK, Hearn JP 1977 Effects of immunization against luteinising hormone releasing hormone on reproduction of the marmoset monkey *Callithrix jacchus*. Nature 265:746–748.

Vickery BH, McRae GI, Stevens VC 1981 Suppression of luteal and placental function in pregnant baboons with agonist analogs of luteinizing hormone–releasing hormones. Fert Steril 36:664–668.

Das C, Talwar GP 1983 Pregnancy–terminating action of a luteffiizing hormone–releasing hormone agonist D–Ser(But)6desGlylOProEA in baboons. Fert Steril 39:218–223.

Rao AJ, Chakraborti R, Kotagi SG, Ravindranath N, Moudgal NR 1985 Effect of LHRH agonists and antagonists in male and female bonnet monkeys (Macaca Radiata). J Steroid Biochem 23:807–809.

Tamada T, Akabori A, Konuma S, Araki S 1976 Lack of release of human chorionic gonadotropin by gonadotropin–releasm'g hormone. Endocrinol Jpn 23:531–533.

Perez–Lopez FR, Robert J, Teijeiro J 1984 Prl, TSH, FSH, b–hCG and oestriol responses to repetitive (triple) LRH/TRH administration in the third trimester of human pregnancy. Acta Endocrinol 106:400–404.

Egyed J, Gati 1 1985 Elevated serum hCG level after intravenous LH–RH administration in human pregnancies. Endocrmiol Exp 19:11–15.

Iwashita M, Kudo Y, Shinozaki Y, Takeda Y 1993 Gonadotropin–releasing hormone increases serum human chorionic gonadotropin in pregnant women. Endocrine Journal 40:539–544.

Kol S, Adashi EY 1995 Intraovarian factors regulating ovarian function. Curr Opin Obstet Gynecol 7:209–213.

Adashi EY 1994 Long–term gonadotropin–releasing hormone agonist therapy: the evolving issue of steroidal 'add–back' paradigms. Hum Reprod 9:1380–1397.

Devreker F, Govaerts 1, Bertrand E, Van den Bergh M, Gervy C, Englert Y 1996 The long–acting gonadotropin–releasing hormone analogues impaired the implantation rate. Fert Steril 65:122–126.

Siler–Khodr TM, Khodr GS, Valenzuela G, Rhode J 1986 Gonadotropin–releasing hormone effects on placental hormones during gestation: II. Progesterone, estrone, estradiol and estriol. Biol Reprod 34:255–264.

Theresa M, Siler–Khodr, Thomas J. Kuehl, Brian H. Vickery, 1984 Effects of a Gonadotropin–releasing hormone antagonist on hormonal levels in the pregnant baboon and on fetal outcome. Fertility and Sterility 41:3.

Theresa M. Siler–Khodr, Endocrine and Paracrine Function of the Human Placenta. Chapter 7, pp. 74–85. RA Polin and W.W. Fox (eds.), WB. Sauders, Philadelphia, 1992.

T. M. Siler–Khodr, I. A. Kang & G. S. Kohdr 1991 current Topic: Symposium on Placental Endocrinology—1. Effects of chorionic GNRH on Intrauterine Tissues and Pregnancy. Bailliere Tindall Ltd. pp. 91–103.

Y. Zohar, A. Elizur, N. M. Sherwood, J.F.P. Powell, J. E. Rivier and N. Zmora, 1995 Gonadotropin–Releasing Activities of the Three Native Forms of Gonadotropin–Releasing Hormone Present in the Brain of Gilthead Seabream. *Sparus aurata*, General and Comparative Endocrinology 97, 289/399.

Xin–Wei Lin and Richard E. Peter, 1997 Cloning and Expression Pattern of a Second [Histhu$^5$Trp$^7$Tyr$^8$] Gonadotropin–Releasing Hormone (Chicken GnRH–II) mRNA in Goldfish: Evidence for Two Distinct Genes, General and Comparative Endocrinology 170, 262–272.

Helge Klungland, James B. Lorens, Oivind Andersen, Gunn O. Kisen and Peter Alestrom 1992 The Atlantic salmon preprio–gonadotropin releasing hormone gene and MRNA, Molecular and Cellular Endocrinology, 84: 167–174.

CHICKEN GNRH ANALOGS AND USES THEREOF IN REGULATION OF FERTILITY AND PREGNANCY

FIELD OF THE INVENTION

The present invention relates generally to the field of regulating fertility and parturition. More particularly, it concerns the use of unique non-mammalian peptide hormone analogs of GnRH designed to be useful in fertility regulation, post-coital contraception and as a menses-inducing agent.

BACKGROUND OF THE INVENTION

Before the chemical characterization of the mammalian hypothalamic GnRH, it was realized that hypothalamic substances regulated production of pituitary LH and FSH. Burgus R., Guillemim R 1970 Hypothalamic releasing factors Ann Rev Biochem 39:499–526. Current contraceptive methods are centered on the existing knowledge of GnRH-gonadotropin-ovarian physiology.

The delineation of mammalian GnRH made possible the ability to create methods to detect and quantify this molecule. The human placenta and the chorionic membranes have also been observed to contain a GnRH-like substance. Gibbons J M, Mitnick M, Chieffo V 1975 In vitro biosynthesis, of TSH- and LH-releasing factors by the human placenta. Am J Obstet Gynecol 121:127–131. The present investigator has recently localized, quantified and demonstrated the synthesis of a GnRH-like substance by the human placenta. Siler-Khodr T M, Khodr G S 1978 Luteinizing hormone releasing factor content of the human placenta. Am J Obstet Gynecol 130:216–219; Khodr G S, Siler-Khodr T M 1978 Localization of luteinizing hormone releasing factor (LRF) in the human placenta. Fert Steril 29:523–526; Siler-Khodr T M, Khodr G S 1979 Extrahypothalamic luteinizing hormone releasing factor (LRF): Release of immunoreactive LRF by the human placenta in vitro. Fert Steril 22:294–296; Khodr G S, Siler-Khodr T M 1980 Placental LRF and its synthesis. Science 207:315–317.

The concentration of immunoreactive GnRH-like material in the placenta and maternal blood has been found to vary with gestational age, following a pattern similar to that of hCG Siler-Khodr T M, Khodr G S, Valenzuela G 1984 Immunoreactive gonadotropin-releasing hormone level in maternal circulation throughout pregnancy. Am J Obstet Gynecol 150:376– 379; Sorein K A, Smilde C B, Spencer D K, Yoder B A, Grayson M A, Siler-Khodr T M 1996 Circulating maternal CRH and GnRH in normal and abnormal pregnancies. Am J Obstet Gynecol 175:912–916. It was also demonstrated that exogenous synthetic mammalian GnRH can stimulate hCG production from human placental explants in vitro, and that the GnRH stimulation of hCG release was a receptor mediated event, since it was specific and could be inhibited by a GnRH antagonist, [N-Ac-Pro, D-P-Cl-Phe, D-Nal(2)]-GnRH. Burgus R., Guillemim R 1970 Hypothalamic releasing factors Ann Rev Biochem 39:499–526; Baba Y, Matsui H, Schally A V 1971 Structure of the porcine LH- and FSH-releasing hormone II Confirmation of the proposed structure by conventional sequential analyses Biochem Biophys Res Commun 44:459–463; Gibbons J M, Mitnick M, Chieffo V 1975 In vitro biosynthesis, of TSH- and LH-releasing factors by the human placenta. Am J Obstet Gynecol 121:127–131; Siler-Khodr T M, Khodr G S 1979 Extrahypothalamic luteinizing hormone releasing factor (LRF): Release of immunoreactive LRF by the human placenta in vitro. Fert Steril 22:294–296; Siler-Khodr T M, Khodr G S, Vickery B H, Nestor J J, Jr. 1983 Inhibition of hCG, alpha hCG and progesterone release from human placental tissue in vitro by a GnRH antagonist. Life Sci 32:2741–2745, Khodr G S, Siler-Khodr T M 1979 the effect of luteinizing hormone releasing factor (LRF) on hCG secretion Fert Steril 30:301–304; Siler-Khodr T M, Khodr G S 1981 Dose response analysis of GnRH stimulation of hCG releases from human term placenta. Biol Reprod 25:353–358; Siler-Khodr T M, Khodr G S 1978 Luteinizing hormone releasing factor content of the human placenta. Am J Obstet Gynecol 130:216–21; Khodr G S, Siler-Khodr T M 1978 Localization of luteinizing hormone releasing factor (LRF) in the human placenta. Fert Steril 29:523–526. In addition to the inhibition of hCG, progesterone production was dramatically suppressed. The present investigator also observed that hCG response was related to the gestational age of the placenta. Siler-Khodr T M, Khodr G S, Valenzuela G, Rhode J 1986 Gonadotropin-releasing hormone effects on placental hormones during gestation: 1 Alpha-human chorionic gonadotropin, human chorionic gonadotropin and human chorionic somatomammotropin. Biol Reprod 34:245–254. In addition, a gestational age-related action of the GnRH antagonist on the release of hCG and steroids was observed. Siler-Khodr T M, Khodr G S, Rhode J, Vickery B H, Nestor J J, Jr. 1987 Gestational age related inhibition of placental hCG, hCG and steroid hormone release in vitro by a GnRH antagonist. Placenta 8:1–14. Further studies demonstrated a potent action of GnRH on placental prostanoids, again resulting in their inhibition when endogenous chorionic GnRH was the highest. Siler-Khodr T M, Khodr G S, Valenzuela G, Harper J, Rhode J 1986 GnRH effects on placental hormones during gestation. 111 Prostaglandin E, prostaglandin F, and 13,14-dihydro-15-keto-prostaglandin F. Biol Reprod 35:312–319; Kang I S, Koong M Y, Forman J S, Siler-Khodr T M 1991 Dose-related action of GnRH on basal prostanoid production from the human term placenta. The 38th Annual Meeting of the Society for Gynecologic Investigation (San Antonio) Abstract #310:253 (Abstr.). The GnRH antagonist also inhibited basal prostaglandin production with greater potency than equimolar concentrations of GnRH, and this action was partially conserved by mammalian GnRH. Siler-Khodr T M, Khodr G S, Harper M J, Rhode J, Vickery B H, Nestor J J, Jr. 1986 Differential inhibition of human placental prostaglandin release in vitro by a GnRH antagonist. Prostaglandins 31:1003–1010. A chorionic GnRH was identified by the present investigator to regulate hCG in a paracrine fashion within the human placenta. Siler-Khodr T.M. and G. S. Khodr. 1981. The production and activity of placental releasing hormones. In Fetal Endocrinology. J. Resko and W. Montagna, editors. Academic Press Inc. New York. 183–210; Siler-Khodr, T. M. and G. S. Khodr. 1982 GnRH in the placenta. In role of Peptides and Proteins in Control of Reproduction. D. S. Khindsa and S. M. McCann, editors. Elsevier North Holland, New York. 347–363; Siler-Khodr T M 1983 Hypothalamic-like releasing hormones of the placenta. Clin Perinatol 10:533–566; Siler-Khodr T M 1983 Hypothalamic-like peptides of the placenta. Semin Reprod Endocrinol 1:321–333. These data demonstrated that this paracrine axis is of physiologic significance in cell to cell communication, and not of inconsequential, ectopic, tumor production.

Studies of other investigators have reported on the actions of mammalian GnRH on placental function. The chorionic GnRH axis has also been identified as having an observed feedback interaction for activin, inhibit, follistatin, neurotransmitter, prostaglandin and steriods, Shi L Y, Zhang Z W, Li W X 1994 Regulation of human chorionic gonadotropin secretion and messenger ribonucleic acid levels by follistatin in the NUCC-3 choriocarcinoma cell line. Endocrinology 134:2431–2437; Steele G L, Currie W D, Yuen B H, Jia X C, Perlas E, Luang P C 1993 Acute stimulation of human chorionic gonadotropin secretion by recombinant human activin-A in first trimester human trophoblast. Endocrinology 133:297–303; Li W, Olofsson J I, Jeung E B, Krisinger J, Yuen B H, Leung P C 1994 Gonadotropin-releasing hormone (GnRH) and cyclic AMP positively regulate inhibit subunit messenger RNA levels in human placental cells. Life Sci 55:1717–1724; Petraglia F, Vaughan J, Vale W 1991 Inhibin and activin modulate the release of gonadotropin-releasing hormone, human chorionic gonadotropin, and progesterone from cultured human placental cells. Proc Natl Acad Sci U S A 86:5114–5117; Petraglia F, Sawchenko P, Lim A T W, Rivier J, Vale W 1987 Localization, secretion, and action of inhibit in human placenta. Science 237:187–189; Shi C Z, Zhuang L Z 1993 Norepinephrine regulates human chorionic gonadotropin production by first trimester trophoblast tissue in vitro. Placenta 14:683–693; Cemetikic B, Maulik D, Ahmed M S 1992 Opioids regulation of hCG release from trophoblast tissue is mediated by LHRH. Placenta Abstract: 9(Abstr.); Petraglia F, Vaughan J, Vale W 1990 Steroid hormones modulate the release of immunoreactive gonadotropin-releasing hormone from cultured human placental cells. J Chn Endocrinol Metab 70:1173–1178; Haning RV, Jr., Choi L, Kiggens A J, Kuzma D L, Summerville J W 1982 Effects of dibutyryl adenosine 3', 5'-monophosphate, luteinizing hormone-releasing hormone, and aromatase inhibitor on simultaneous outputs of progesterone 17b-estradiol, and human chorionic gonadotropin by term placental explants. J Clin Endocrinol Metab 55:213–218; Petraglia F, Lim A T, Vale W 1987 Adenosine 3', 5-monophosphate, prostaglandin, and epinephrine stimulate the secretion of immunoreactive gonadotropin-releasing hormone from cultured human placental cells. J Clin Endocrinol Metab 65:1020–1025; Harting R V, Jr. Choi L, Kiggens A J, Kuzma D L 1982 Effects of prostaglandin, dibutyryl camp LHRH, estrogen, progesterone, and potassium on output of prostaglandin F2a, 13,14-dihydro-15-keto-prostaglandin F2a, hCG, estradiol, and progesterone by placental minces. Prostaglandins 24:495–506; Barnea E P, Feldman D, Kaplan M 1991. The effect of progesterone upon first trimester trophoblastic cell differentiation and human chorionic gonadotropin secretion. Hum Reprod 6:905–909; Barnea E R, Kaplan M 1989 Spontaneous, gonadotropin-releasing hormone-induced, and progesterone-inhibited pulsatile secretion of human chorionic gonadotropin in the first trimester placenta in vitro. J Clin Endocrinol Metab 69:215–217; Branchaud C, Goodyear C, Lipowski L 1983 Progesterone and estrogen production by placental monolayer cultures: Effect of dehydroepiandrosterone and luteinizing hormone-releasing hormone. J Chn Endocrinol Metab 56:761–766; Ahmed N A, Murphy B E 1988. The effects of various hormones on human chorionic gonadotropin production 'in early and late placental explant cultures. Am J Obstet Gynecol 159:1220–1227; Iwashita M, Watanabe M, Adachi T, Ohira A, Shinozaki Y, Takeda Y, Sakamoto S 1989 Effect of gonadal steroids on gonadotropin-releasing hormones stimulated human chorionic gonadotropin release by trophoblast cells. Placenta 10:103–112; Haning R V, Jr., Choi L, Kiggnes A J, Kuzma D L, Summerville J W 1982 Effects of dibutyryl cAMP, LHRH, and aromatase inhibitor on simultaneous outputs of prostaglandin F2a, and 13, 14-dihydro-15-keto-prostaglandin F2a by term placental explants. Prostaglandins 23:29–40; Wilson E, Jawad M 1980 Luteinizing hormone-releasing hormone suppression of human placental progesterone production. Fert Steril 33:91–93. These and other studies established the presence of this paracrine axis, including a negative feedback loop for progesterone and estrogen, similar to that of the hypothalamic-pituitary-gonadal axis. This placental axis, multiple paracrine axes for GnRH and other hypothalamic-like releasing and inhibiting activities have now been defined in the placenta, eye, pancreas, ovary, brain, bone, etc., and are now recognized as essential to normal physiologic functions. Siler-Khodr, T. M. 1992 The Placenta: Part IV-Function of the Human Placenta. In Neonatal and Fetal Medicine. R. A. Polin and W. W. Fox, editors. W. B. Saunders Co. Philadelphia, Pa. 74–86; Youngblood W W, Hurnni J, Kizer J S 1979 TRH-like immunoreactivity in rat pancreas and eye, bovine and sheep ideals, and human placenta: Non-identity with synthetic Pyroglu-His-Pro-NH$_2$ (TRH). Brain Res 163: 10 1–110; Dubois MP 1975 Immunoreactive somatostatin is present in discrete cells of the endocrine pancreas. Proc Natl Acad Sci USA 72:1340–1343; Adashi. E. Y. 1996. The Ovarian Follicular Apparatus. In Lippincott-Raven Publishers. E. Y. Adashi. J. A. Rock, and Z. Rosenwaks, editors. Lippincott-Raven Publishers, Philadelphia. 17–40.

Recent studies have led to the isolation and characterization of a GnRH gene in the placenta, which is identical to that in the hypothalamus with the exception of the inclusion of the first intron and a very long first exon. Radovick S, Wondisford F E, Nakayama Y, Yamada M, Cutler G B, Jr., Weintraub B D 1990 Isolation and characterization of the human gonadotropin-releasing hormone gene in the hypothalamus and placenta. Mol Endocrinol 4:476–480; Adelman J P, Mason A J, Hayflick J S, Seeburg P H 1986 Isolation of the gene and hypothalamic cDNA for the common precursor of gonadotropin-releasing hormone and prolactin release-inhibiting factor in human and rat. Proc Natl Acad Sci USA 83:179–183; Seebirg P H, Adelman J P 1984 Characterization of cDNA for precursor of human luteinizing hormone releasing hormone. Nature 311:666–668. The message has been localized to the syncytio- and cytotrophoblast, as well as the stroma of the placenta, and is present in higher concentrations during the first half of pregnancy. Duello T M, Tsai S J, Van Ess P J 1993 In situ demonstration and characterization of pro gonadotropin-releasing hormone messenger ribonucleic acid in first trimester human placentas. Endocrinology 133:2617–262–3; Kelly A C, Rodgers A, Dong K W, Barrezueta N X, Blum M, Roberts J L 1991 Gonadotropin-releasing hormone and chorionic gonadotropin gene expression in human placental development DNA Cell Biol 10:411–421. Multiple transcription sites have been identified for the GnRH gene in reproductive tissues, including the placenta. Dong K W, Yu K L, Roberts J L 1993 Identification of a major up-stream transcription start site for the human pro gonadotropin-releasing hormone gene used in reproductive tissues and cell lines. Mol Endocrinol 7:1654–166; Dong K W, Duval P, Zeng Z, Gordon K, Williams R F, Hodgen G D, Jones G, Kerdelhue B, Roberts J L 1996 Multiple transcription start sites for the GnRH gene in rhesus and cynomolgus monkeys: a non-human primate model for studying GnRH gene regulation. Mol Cell Endocrinol 117:121–130; Dong K W, Yu K L, Chen Z G, Chen Y D, Roberts J L 1997 Characterization of multiple promoters directing tissue-specific expression of the human gonadotropin-releasing hormone gene. Endocrinology 138:2754–2762. Steroid regulatory sites on the promoter have also been identified. Chandran U R, Attardi B, Friedman R, Dong K W, Roberts J L, DeFranco D B 1994 Glucocorticoid receptor-mediated repression of gonadotropin-releasing hormone promoter Activity in GTI hypothalamic cell lines. Endocrinology 134:1467–1474; Dong K W, Chen Z G, Cheng K W, Yu K L 1996 Evidence for estrogen receptor-mediated regulation of human gonadotropin-releasing hormone promoter activity in human placental cells. Mol Cell Endocrinol 117:241–246. The functionality of this promoter is supported by showing that GnRH mRNA can be regulated by steroids. Joss J M, King J A, Millar R P 1994 Identification of the molecular forms of and steroid hormone response to gonadotropin-releasing hormone in the Australian lungfish Neoceratodus forsteri. Gen Comp Endocrinol 96:392–400; Montero M, Le Belle N, King J A, Millar R P, Dufour S 1995 Differential regulation of the two forms of gonadotropin-releasing hormone (mGnRH and chorionic GnRH-11) by sex steroids in the European female silver eel (Anguilla anguilla). Neuroendocrinology 61:525–535; Ikeda M, Taga M, Sakakibara H, Minaguchi H, Ginsburg E, Vonderhaar B K 1996 Gene expression of gonadotropin-releasing hormone in early pregnant rat and steroid hormone exposed mouse uteri. J Endocrinol Invest 19:708–713; Gothilf Y, Meiri I, Elizur A, Zohar Y 1997 Preovulatory changes in the levels of three gonadotropin-releasing hormone-encoding messenger ribonucleic acids (mRNSs), gonadotropin. B-submit mRNAs plasma gonadotropin, and steroids in the female gilthead seabream, Spar-us aurata. Biol Reprod 57:1145–1154.

It has previously been accepted that only non-mammalian vertebrates have multiple forms of GnRH in the same species. However, Dellovad, et al. and in 1994, King et al. have described Chicken II GnRH in shew, mole and bat brain, thus demonstrating that two different isomers of GnRH existed in the mammal. Dellovad T L, King J A, Millar R P, Rissman E F 1993 Presence and differential distribution of distinct forms of immunoreactive gonadotropin-releasing hormone in the musk shrew brain. Neuroendocrinology 58:166–177; King J A, Steneveld A A, Curlewis J D, Rissman E F, Millar R P 1994 Identification of chicken GnRH H in brains of inetatherian and early-evolved eutherian species of mammals. Regul Pept 54:467–477. Even then, it was still thought that in modern placental mammalian species, the existence of different GnRHs did not occur. Therefore, the hypothesis of more than one form of GnRH in the human placenta was considered dubious. Chicken II GnRH has now been characterized in the guinea pig and in the human brain. Jimenez-Linan M, Rubin B S, King J C 1997 Examination of guinea pig luteinizing hormone-releasing hormone gene reveals a unique decapeptide and existence of two transcripts in the brain. Endocrinology 13 8:4123–4130; Lescheid D, Terasawa E, Abler L A, Urbanski H F, Warby C M, Millar R P, Sherwood N M 1997 A second form of gonadotropin-releasing hormone (GnRH) with characteristics of chicken GnRH-11 is present in the primate brain. Endocrinology 138:1997. Separate genes for Chicken II GnRH and mammalian GnRH have also been described. White S A, Bond C T, Francis R C, Kasten T L, Fernald R D, Adelman J P 1994 A second gene for gonadotropin-releasing hormone: cDNA and expression pattern in the brain. Proc Natl Acad Sci USA 91:1423–1427; Lin X W, Peter R E 1997 Cloning and expression pattern of a second [His5Trp7Tyr81gonadotropin-releasing hormone (chicken GnRH-H-11) mnRNA in goldfish; evidence for two distinct genes. Gen Comp Endocrinol 107:262–272.

The GnRH in the placenta has not been characterized as fully as the GnRH receptor in the pituitary. Sealfon S C, Weinstein H, Millar R P 1997 Molecular mechanism of ligand interaction with the gonadotropin-releasing hormone receptor. Endocr Rev 18:180–205; Karten M J, Rivier J E 1986 Gonadotropin-releasing hormone analog design. Structure-friction studies toward the development of agonists and antagonists: Rationale and perspective. Endocr Rev 7:44–66 It is known that two populations of placental GnRH receptors exist, one having a Ka of $10^{-9}M$ and the other with a significantly lower affinity of $10^{-7}M$. In addition, superagonist or antagonist for the pituitary GnRH receptor shows very different affinity for the placental receptor. Escher E, Mackiewicz Z, Lagace G, Lehoux J, Gallo-Payet N, Bellabarba D, Belisle S 1988 Human placental LHRH receptor: Agonist and antagonist labeling produces differences in the size of the non-denatured, solubilize receptor. J Recept Res 8:391–405; Bramley T A, McPhie C A, Menzies G S 1992 Human placental gonadotropin-releasing hormone (GnRH) binding sites: 1 Characterization, properties and ligand specificity. Placenta 12:555–581. Other isomers of GnRH, such as salmon GnRH and Chicken II GnRH, have a much greater affinity for the placental receptor, yet bind with a lesser affinity to the human pituitary receptor. Bramley T A, McPhie C A, Menzies G S 1992 Human placental gonadotropin-releasing hormone (GnRH) binding sites: 1 Characterization, properties and ligand specificity. Placenta 12:555–581. These data demonstrate the existence of a specific placental receptor for GnRH-like molecules, yet the true ligand for this receptor is not known.

In amphibians, a Chicken II GnRH receptor as well as a mammalian GnRH receptor have been shown. The specificity and evolutionary aspects of the GnRH receptor have been studied in many species. Mammalian GnRH has been reported to be active in many vertebrate classes. Other GnRHs, such as Chicken II GnRH and salmon GnRH, have reduced affinity for the mammalian pituitary receptor.

GnRH receptor activity, as well as the mRNA for the GnRH receptor, varies throughout gestation in the human placenta. Bramley T A, McPhie C A, Menzies G S 1994 Human placental gonadotropin-releasing hormone (GnRH) binding sites: 111. Changes in GnRH binding levels with stage of gestation. Placenta 15:733–745; Lin L S, Roberts V J, Yen S S 1997 Expression of human gonadotropin-releasing hormone receptor gene in the placenta and its functional relationship to human chorionic gonadotropin secretion. J Clin Endocrinol Metab 80:580–585. The receptor is greatest in early gestation and appears to be down regulated by 12–20 weeks. While the receptor is again detectable in term placentas, the mRNA (using a GnRH decapeptide probe and in situ hybridization methodology) was undetectable at this state of gestation. Bramley T A, McPhie C A, Menzies G S 1994 Human placental gonadotropin-releasing hormone (GnRH) binding sites: 111. Changes in GnRH binding levels with stage of gestation. Placenta 15:733–745; Lin L S, Roberts V J, Yen S S 1997 Expression of human gonadotropin-releasing hormone receptor gene in the placenta and its functional relationship to human chorionic gonadotropin secretion. J Clin Endocrinol Metab 80:580–585. This pattern of receptor activity is consistent with the concentration of GnRH-like material in placental tissue and maternal blood throughout gestation, and supports the hypothesis that chorionic GnRH may down-regulate its chorionic receptors, as can mammalian GnRH, and its analogs at the pituitary level. Siler-Khodr T M, Khodr G S, Valenzuela G 1984 Immunoreactive gonadotropin-releasing hormone level in maternal circulation throughout pregnancy. Am J Obstet Gynecol 150:376–379; Siler-Khodr T M, Khodr G S 1978 Luteinizing hormone releasing factor content of the human placenta. Am J Obstet Gynecol 130:216–219. Studies by the present investigator and those of Barnea et al, have demonstrated competitive inhibition by GnRH antagonist. Siler-Khodr T M, Khodr G S, Vickery B H, Nestor J J, Jr. 1983 Inhibition of hCG, alpha hCG and progesterone release from human placental tissue in vitro by a GnRH antagonist. Life Sci 32:2741–2745; Siler-Khodr T M, Khodr G S, Harper M J, Rhode J, Vickery B H, Nestor J J, Jr. 1986 Differential inhibition of human placental prostaglandin release in vitro by a GnRH antagonist. Prostaglandins 31:1003–1010; Barnea E R, Kaplan M, Naor Z 1991 Comparative stipulatory effect of gonadotropin releasing hormone (GnRH) and GnRH agonist upon pulsatile human chorionic gonadotropin secretion in superfused placental explants: reversible inhibition by a GnRH antagonist. Hum Reprod 6:1063–1069. Other studies of Szilagyi et al. and Currie et al. indicate that pituitary GnRH agonist can down-regulate the placental GnRH receptor. Szilagyi A, Benz R, Rossmanith W G 1992. The human first-term placenta in vitro: regulation of hCG secretion by GnRH and its antagonist. Gynecol Endocrinol 6:293–300; Currie W D, Setoyarna T, Lee P S, Baimbridge K G, Church J, Yuen B H, Leung P C 1993 Cytosolic free $Ca^{2+}$ in human syncytiotrophoblast cells increased by gonadotropin-releasing hormone. Endocrinology 133:2220–2226. In addition, the demonstration that the placental GnRH receptor can be up regulated in cell cultures by estradiol supports the hypothesis that this receptor is functional in the regulation of placental hormonogenesis. Barnea E R, Kaplan M, Naor Z 1991 Comparative stipulatory effect of gonadotropin releasing hormone (GnRH) and GnRH agonist upon pulsatile human chorionic gonadotropin secretion in superfused placental explants: reversible inhibition by a GnRH antagonist. Hum Reprod 6:1063–1069; Bliatacharya S, Chaudhary J, Das C 1992 Responsiveness to gonadotropin releasing hormone of human term trophoblast cells in vitro: induction by estradiol. Biochein Int 28:363–371.

Another factor that regulates a hormone's activity is its metabolism. The enzyme that degrades GnRH differs during pregnancy from the enzyme that degrades GnRH in the pituitary or the blood of non-pregnant individuals. In placental tissue, the primary enzymatic activity for the degradation of GnRH is chorionic peptidase-1 (C-ase-1), a post-proline peptidase. C-ase-1 is a glycoprotein with a molecular weight of 60,000. Siler-Khodr T M, Kang I S, Jones M A, Harper M J K, Khodr G S, Rhode J 1989 Characterization and purification of a placental protein that inactivates GnRH, TRH and Angiotensin 11. Placenta 10:283–296; Kang I S, Siler-Khodr T M 1992 Chorionic peptidase miactiviates GnRH as a post-proline peptidase. Placenta 13:81–87. It acts as a post-proline peptidase, and is inhibited by bacitracin, para-amino-benzamidine, acetopyruvate and certain cations. Siler-Khodr T M, Kang I S, Jones M A, Harper M J K, Khodr G S, Rhode J 1989 Characterization and purification of a placental protein that inactivates GnRH, TRH and Angiotensin 11. Placenta 10:283–296. GnRH is actively degraded by C-ase-1 at neutral pH, having a Km of $10^{-8}$M. Kang I S, Gallwitz J, Guzman V, Siler-Khodr T M 1990. Definition of the enzyme kinetics and optimal activity of chorionic peptidase-1. The $23^{rd}$ Annual Meeting of the Society for the Study of Reproduction (Vancouver) (Abstract #311):144(Abstr.). Using immunofluorescent methodology, C-ase-1 has been localized by the present inventor in the cytoplasm of the syncytiotrophoblast and syncytial buds. It is secreted into maternal blood, where GnRH is not stable without specific inhibitors of this post-proline peptidase. Benuck M, Marka N 1976 Differences in the degradation of hypothalamic releasing factors by rat and human serum. Life Sci 19:1271–1276. C-ase-1 is present in very high concentrations, and accounts for virtually all GnRH degrading activity in the placenta under physiological conditions.

These in vitro studies support the hypothesis of the specific, receptor-mediated and enzyme-regulated action of mammalian GnRH on placental hormonogenesis, and demonstrate the paracrine effects and feedback interactions for numerous intrauterine hormones interacting with chorionic GnRH. Further studies on the action of mammalian GnRH and its analogs in vivo have also demonstrated these paracrine interactions for chorionic GnRH-like activity and numerous other chorionic hormones, and have established the physiologic role of GnRH in the maintenance of normal pregnancy. Siler-Khodr, T. M. 1993. Luteinizing Hormone Releasing Hormone (LHRH) and the Placenta and Fetal Membranes. In Molecular Aspects of Placental and Fetal Membrane Autocoids. G. E. Rice and S. P. Brennecke, editors. CRC Press, Inc. Ann Arbor. 339–350; Petraglia F, Calza L, Garuti G C, Giardino L, De Ramundo B M, Angioni S 1990. New aspects of placental endocrinology. J Endocrinol Invest 65:262–267.

Recent studies demonstrate that the number of GnRH receptors and mRNA for the GnRH receptor in the placenta varies in a pattern similar to that of hCG.Duello T M, Tsai S J, Van Ess P J 1993. In situ demonstration and characterization of pro gonadotropin-releasing hormone messenger ribonucleic acid in first trimester human placentas. Endocrinology 133:2617–2623; Lin L S, Roberts V J, Yen S S 1997. Expression of human gonadotropin-releasing hormone receptor gene in the placenta and its functional relationship to human chorionic gonadotropin secretion. J Clin Endocrinol Metab 80:580–585. Other investigators have shown steroid responsive elements in the placental GnRH gene, providing further evidence for the physiologic regulation of placental GnRH-like activity. Dong K W, Chen Z G, Cheng K W, Yu K L 1996 Evidence for estrogen receptor-mediated regulation of human gonadotropin-releasing hormone promoter activity in human placental cells. Mol Cell Endocrinol 117:241–246. Petraglia et al. has described the pulsatile release of a GnRH-like substance, which has a specific pulse frequency, amplitude and duration, with increased amplitude during early gestation. Petraglia F, Genazzani A D, Aguzzoli L, Gallinelli A, de Vita D, Caruso A, Genazzani A R 1994. Pulsatile fluctuations of plasma-gonadotropin-releasing hormone and corticotropin-releasing factor levels in healthy pregnant women. Acta Obstet Gynecol Scand 73:284–289. Other investigators using Rhesus monkey embryos have demonstrated the secretion of a GnRH-like substance by the peri-implantation embryo, which precedes the secretion of chorionic gonadotropin. Seshagiri P B, Terasawa E, Heam J P 1994. The secretion of gonadotropin-releasing hormone by peri-implantation embryos of the rhesus monkey: comparison with the secretion of chorionic gonadotropin. Hum Reprod 9:1300–1307.

Other investigators have shown that administration of high doses of mammalian GnRH, its agonistic analogs or antibodies, to pregnant baboons and monkeys effects a sharp decrease of CG production and progesterone, which in most cases leads to termination of pregnancy. Gupta S K, Singh M 1985 Characteristics and bioefficacy of monoclonal anti-gonadotropin releasing hormone antibody. Am J. Repro Immunol Microbiol 7:104–108; Das C, Gupta S K, Talwar G P 1985 Pregnancy interfering action of LHRH and anti-LHRH. J. Steroid Biochem 23:803–806; Hodges J K, Hearn J P 1977 Effects of immunization against luteinizing hormone releasing hormone on reproduction of the marmoset monkey *Callithrix jacchus*. Nature 265:746–748; Vickery B H, McRae G I, Stevens V C 1981 Suppression of luteal and placental function in pregnant baboons with agonist analogs of luteinizing hormone-releasing hormones. Fert Steril 36:664–668; Das C, Talwar G P 1983 Pregnancy-terminating action of a luteinizing hormone-releasing hormone agonist D-Ser(But)6desGlylOProEA in baboons. Fert Steril 39:218–223; Rao A, Moudgal N 1984 Effect of LHRH injection on serum chorionic: gonadotropin levels in the pregnant bonnet monkey (Macaca radiata). Obstet Gynecol 12:1105–1106; Rao A J, Chakraborti R, Kotagi S G, Ravindranath N, Moudgal N R 1985 Effect of LHRH agonists and antagonists in male and female bonnet monkeys (Macaca Radiata). J. Steroid Biochem 23:807–809. Interruption of pregnancy was most consistently observed when these mammalian GnRH analogs were administered following implantation. In pregnant women, administration of low doses of mammalian GnRH does not significantly change circulating hCG. Tamada T, Akabori A, Konuma S, Araki S 1976 Lack of release of human chorionic gonadotropin by gonadotropin-releasing hormone. Endocrinol Jpn 23:531–533; Perez-Lopez F R, Robert J, Teijeiro J 1984 Prl, TSH, FSH, B-hCG and oestriol responses to repetitive (triple) LRH/TRH administration in the third trimester of human pregnancy. Acta Endocrinol 106:400–404. However, this finding was dose and gestational age related. Egged J, Gati 1 1985 Elevated serum hCG level after intravenous LH-RH administration in human pregnancies. Endocrinol Exp 19:11–15; Iwashita M, Kudo Y, Shinozaki Y, Takeda Y 1993 Gonadotropin-releasing hormone increases serum human chorionic gonadotropin in pregnant women. Endocrine Journal 40:539–544.

A recent study of Devreker et al. reports that the use of long-acting mammalian GnRH analogs in IVF, impaired the implantation rate. Devreker F, Govaerts 1, Bertrand E, Van den Bergh M, Gervy C, Englert Y 1996. The long-acting gonadotropin-releasing hormone analogues impaired the implantation rate. Fert Steril 65:122–126. While these analogs have proven to be generally nontoxic, long-term chronic use has been associated with a hypo-estrogenic state. Accidental administration of mammalian GnRH analogs during early pregnancy has been reported, with varied outcomes. Siler-Khodr, T. M. 1994. Potentials for embryo damage of GnRH analogs. In Ovulation Induction: Basic Science and Clinical Advances. M. Filicor and C. Flamigni, editors Elsevier Science B. V. Amsterdam. 279–306. Generally, pregnancy outcomes appeared unaffected, but increased cases of spontaneous abortion and pre-term labors have also been observed. The varied outcomes may reflect the different doses and protocols of administration of these mammalian GnRH analogs, as well as the different analogs employed. For analogs that can be rapidly metabolized by the chorionic tissues, little effect, if any, would be anticipated. In addition, the affinity for the placental receptor for many of these mammalian GnRH analogs is greatly reduced as compared to the pituitary receptor's affinity. In those case, little chorionic effect would be observed.

SUMMARY OF THE INVENTION

The present invention, in a general and overall sense, relates to novel pharmaceutical preparations that include non-mammalian gonadotropin releasing honnone (GnRH) analogs specifically designed to bind human chorionic GnRH receptor and ovarian GnRH receptors. These analogs are designed to be resistant to degradation by chorionic peptidase 1 (C-ase-1). C-ase-1 has been found to specifically and very actively degrade GnRH in chorionic tissues and maternal blood.

The non-mammalian GnRH analogs of the present invention may act either as a superagonist at the placental receptor leading to its down regulation, or as a pure antagonist of chorionic GnRH at the GnRH receptor. The down-regulation or antagonism of endogenous chorionic GnRH will provide for a reduction in human chorionic gonadotropin (hCG) production. This will also provide a reduction in ovarian and placental steroidogenesis. In addition, a direct ovarian luteolytic action may be expected to occur. If trophoblastic and/or ovarian function is jeopardized, premature luteolytic action might occur. If trophoblastic and/or ovarian function is jeopardized, premature luteolysis of the corpus luteum will occur and menses will ensue. Thus, such an agent may be used as a post-ciotal, luteolytic agent, leading to the induction of menses. Until now, no such GnRH analog has been found to be active during pregnancy or at the ovary.

The inventor has designed non-mammalian GnRH analogs that are active as luteolytic, menses-inducing agents and/or post-coital contraceptives. The chorionic receptor binding activity of these particularly designed non-mammalian GnRH analogs has also been characterized in the development of the present analogs. The analogs of the invention may be further defined as resistant to enzymatic degradation by C-ase-1. The agonist and antagonists with the greatest receptor affinity and tissue stability are expected to effectively inhibit hCG and progesterone release from human placenta. The non-mammalian GnRH analogs of the invention may be used to inhibit placental production of hCG, and have a direct effect on steroidogenesis at the ovary. This physiological effect of the analogs may thus be used to induce luteolysis and menses-induction.

In one aspect, the invention provides methods of synthesizing analogs of non-mammalian GnRH having increased activity in the chorionic tissues. Methods to inhibit hCG production by placental tissues, that in turn provide a reduction of ovarian and placental steroidogenesis, i.e., luteolysis and menses-induction, are provided in another aspect of the present invention. The use of these analogs directly on the ovary is yet another particular embodiment of the invention. The analogs of the invention may be used in pharmaceutical preparations as a menses-regulating agent, a contraceptive, or as an abortifacient.

Non-mammalian chorionic GnRH analogs that are superagonist or antagonists at the trophoblastic/placental level constitute yet other embodiments of the invention. Such a non-mammalian analog would provide for the inhibition of steroidogenesis during pregnancy, acting both as an anti-chorionic and anti-luteal agent by inhibiting steroidogenesis leading to menses induction. The chorionic GnRH analogs of the invention thus comprise peptides that are capable of specifically binding the chorionic and/or ovarian GnRH receptors with high affinity, are resistant to degradation by the C-ase-1 and effect either a down-regulation of the chorionic GnRH receptor or act as a true antagonist, inhibiting hCG production and ovarian and placental steroidogenesis or directly inhibiting ovarian steroidogenesis. In other embodiments, the invention comprises a Salmon or Chicken II GnRH sequence, which both show greater affinity for the placental receptor than mammalian GnRH, that are modified at the C-terminal. An $\alpha$-aza-Gly$^{10}$-NH$_2$ substitution at the 10 position may be used, making the sequence more stable in chorionic tissues and maternal blood. In other embodiments the GnRH analog sequence is substituted at the 6-position with a D-Arg, or other D-amino acid. In yet other embodiments, both of these modifications are made to the GnRH analog peptide sequence. These modifications are expected to enhance the binding of the molecule, while at the same time inhibit any of the endopeptidases that are present in blood. These analogs are expected to have increased binding to the placental or ovarian receptor and increased metabolic stability. The placental receptor binding, placental metabolic degradation and the biological activity for hCG, rogesterone and prostaglandin production was studied for each of these specially designed non-mammalian GnRH analogs, and compared to closely related pituitary mammalian GnRH analogs (Buserilin, typtolein, Leuprolide, etc). These studies demonstrated greater stability of the non-mammalian GnRH analogs, compared to the mammalian GnRH analogs examined.

In other embodiments, the invention provides non-mammalian GnRH analogs with enhanced activity within the intrauterine tissues, as well as a method for regulating hCG production and thus progesterone production during pregnancy. These non-mammalian GnRH analogs may also have a direct action at the ovary. Luteolysis may be affected by a dual mechanism i.e., through inhibition of hCG and thus reduction of ovarian steroidogenesis and/or direct inhibition of ovarian steroidogenesis.

It is envisioned that these analogs will be administered intra-nasally, orally, intramuscularly or vaginally. However, virtually any mode of administration may be used in the practice of the invention. Treatment with these analogs may require one to three days of active non-mammalian GnRH analog when used as a post coital contraceptive. As a monthly contraceptive, the placebo is envisioned to start on the first day of menses and continue for approximately 13 days, then the analog would be given 13 through 28, or less when menses is induced. This could be repeated monthly.

Numerous IVF protocols now routinely use mammalian GnRH analogs for ovulation timing and have been shown to be nontoxic, even after weeks of administration. Long-term therapies with mammalian GnRH analogs have been associated with a Hypoestrogenic State, but in the envisioned modes of administration, exposure would not exceed three days to two weeks. The effect on the pituitary GnRH receptor is expected to be minimal with these non-mammalian GnRH analogs and with this short duration of treatment, the menstrual cycle may not be altered. Thus, the limited time of exposure in the late luteal phase and the specific receptor activity of these analogs make it less likely to interfere with reproductive cyclicity and/or normal physiology. The design of the present non-mammalian analogs considers the specific metabolism of GnRH during pregnancy.

Another embodiment of the invention provides non-mammalian GnRH analogs that are resistant to degradation by C-ase-1. This analog will bind the chorionic GnRH receptor or non-mammalian GnRH with high affinity so to displace the endogenous GnRH-like activity and block its action.

In another aspect, the invention provides more potent non-mammalian GnRH analogs that will specifically bind to the placental and the ovarian GnRH receptor. In addition, analogs will be provided that are stable in maternal circulation and in the blood of non-pregnant individuals. It is also anticipated that these analogs will be biologically active in chorionic tissues and at the ovary in the regulation of hormonogenesis that will affect the maintenance of pregnancy and/or the receptivity of the uterus for implantation. Due to the specificity of these analogs and their relatively short half-life, the present invention provides non-mammalian GnRH analogs.

Other proline-containing peptides compete for C-ase-1 activity, such as angiotensin II, and to a lesser extent, thyrotrophin releasing hormone and reduced oxytocin. Siler-Khodr T M, Kang I S, Jones M A, Harper M J K, Khodr G S, Rhode J 1989 Characterization and purification of a placental protein that inactivates GnRH, TRH and Angiotensin 11. Placenta 10:283–296; Siler-Khodr T M, Grayson M, Pena A, Khodr T 1997. Definition of enzyme specificity of chorionic peptidase-1 for GnRH, TRH, oxytocin and angiotensin 11. J Soc Gynecol Invest 4:129A(Abstr.). The existing mammalian GnRH analogs are also proline-containing molecules. Since human pituitary and blood contain an enzymatic activity that degrades GnRH at the 5–6 position, not at the 9 position, the present non-mammalian GnRH analogs have been designed to inhibit the former enzymatic activities, and have substitutions in the 5–6 position of the molecule. Benuck M, Marka N 1976 Differences in the degradation of hypothalamic releasing factors by rat and human serum. Life Sci 19:1271–1276. The present analogs are therefore, resistant to degradation at the pituitary or in the blood of non-pregnant individuals, but not the placenta or in maternal blood. Millar R P, King J A, Davidson J S, Milton R C 1987 Gonadotropin-releasing hormone-diversity of fictions and clinical applications. S Afr Med J 72:748–755. Substitution of the Gly-NH$_2$ in the 10 position with ethylamide, or the even more potent α-aza-Gly-NH$_2$ in the 10 position, inhibits degradation by post-proline peptidase. Zohar Y, Goren A, Fridkin M, Elhanati E, Koch Y 1990. Degradation of gonadotropin-releasing hormones in the gilthead seabream, Sparus aurata. 11. Cleavage of native salmon GnRH, mammalian LHRH, and their analogs in the pituitary, kidney, and liver. Gen Comp Endocrinol 79:306–319. A number of the existing analogs also have an ethylamide substitution of Gly-NH$_2$ in the position 10.

The stability of the present non-mammalian analogs in the presence of C-ase-1 was also examined. The degradation of four of these analogs was examined using a competitive inhibition assay for GnRH by C-ase-1. While replacement of Gly$^{10}$-NH$_2$ in the 10 position with ethylamide made each of these GnRH analogs more resistant to degradation, some of the analogs still effected a substantial competition with GnRH for C-ase-1 activity. Of four ethylamides studied, des-Gly$^{10}$-GnRH-ethylamide, the des-Gly$^{10}$, D-Leu$^6$, D-Leu$^6$-GnRH-ethylamide, or Buserilin, each were potent inhibitors of GnRH degradation by C-ase-1. For results obtained for des-Gly10-GnRH-ethylamide, see FIG. 6. The less active an analog is as a competitor for GnRH degradation by C-ase-1, the more stable that analog will be in the chorionic tissues and in maternal blood. Thus, the existing mammalian GnRH analogs commonly used in medicine can be degraded in the chorionic tissues.

The initial findings of inhibition can be explained by recognizing that the decapeptide sequences for mammalian GnRH and chorionic GnRH are not identical. Substantial data exists that the receptor and the chemical nature of chorionic GnRH are not identical to GnRH. Postulating that chorionic GnRH differs from the decapeptide, GnRH, and that there is a placental receptor specific for chorionic GnRH, explains the biphasic response of placental hormones. Mammalian GnRH acts as a partial agonist of chorionic GnRH. When receptors are available, it acts as an agonist of chorionic GnRH. When placental receptors are low or occupied, GnRH competes with the more potent chorionic GnRH resulting in an antagonistic action.

GnRH-like substances have been found by the present inventor to be decreased at mid-pregnancy in women who later have pre-term labor, and increased in those with post term deliveries. In more recent studies, a GnRH binding substance has been demonstrated in their circulation and in these cases hCG was abnormally reduced and pregnancy loss was observed. Thus, the current studies of GnRH-like substance production during pregnancy indicate that chorionic GnRH is of significance to the maintenance of normal pregnancy.

Mammalian GnRH analogs, ZOLADEX™ (Goserelin acetate) and Organon 30276, were administered to pregnant baboons via mini-pump on days 14 through 21 post ovulation. The hormonal release and pregnancy outcome was compared to saline treated controls. CG and progesterone decreased, and in most animals pregnancy outcomes were jeopardized. However, using this analog, abortions were not consistently effected, except for the 100 mg–7 day regiment of the Organon antagonist. Further studies with the new designed chorionic GnRH analogs having enhanced receptor activity and chorionic stability promise to provide an even more potent action.

In a dose-response saline-controlled study, a small stimulation of hCG in very early pregnancy was observed by the present inventor. However, an inhibition of hCG and progesterone was observed by 12 weeks of pregnancy when chorionic GnRH is maximal.

The present inventor has found that certain non-mammalian GnRH analogs can act on the chorionic GnRH receptor, and with high affinity binding, affect changes in the intrauterine environment that effect the outcome of pregnancy. This finding is the basis of the invention disclosed herein. Thus, the present investigator has developed particular (non-mammalian) GnRH analogs that can be used for luteolysis and menstrual induction. The ability of specific (non-mammalian) GnRH analogs to interact with the physiologic regulation of hCG, progesterone and prostaglandin during luteal phase of the cycle and early pregnancy, may be used to specifically interrupt luteal function and early pregnancy according to the invention as outlined here.

GnRH 1.000 M, ○ GnRH 0.500 M, ▽ GnRH 0.250 M, ◇ GnRH 0.125 M

Figure 4:
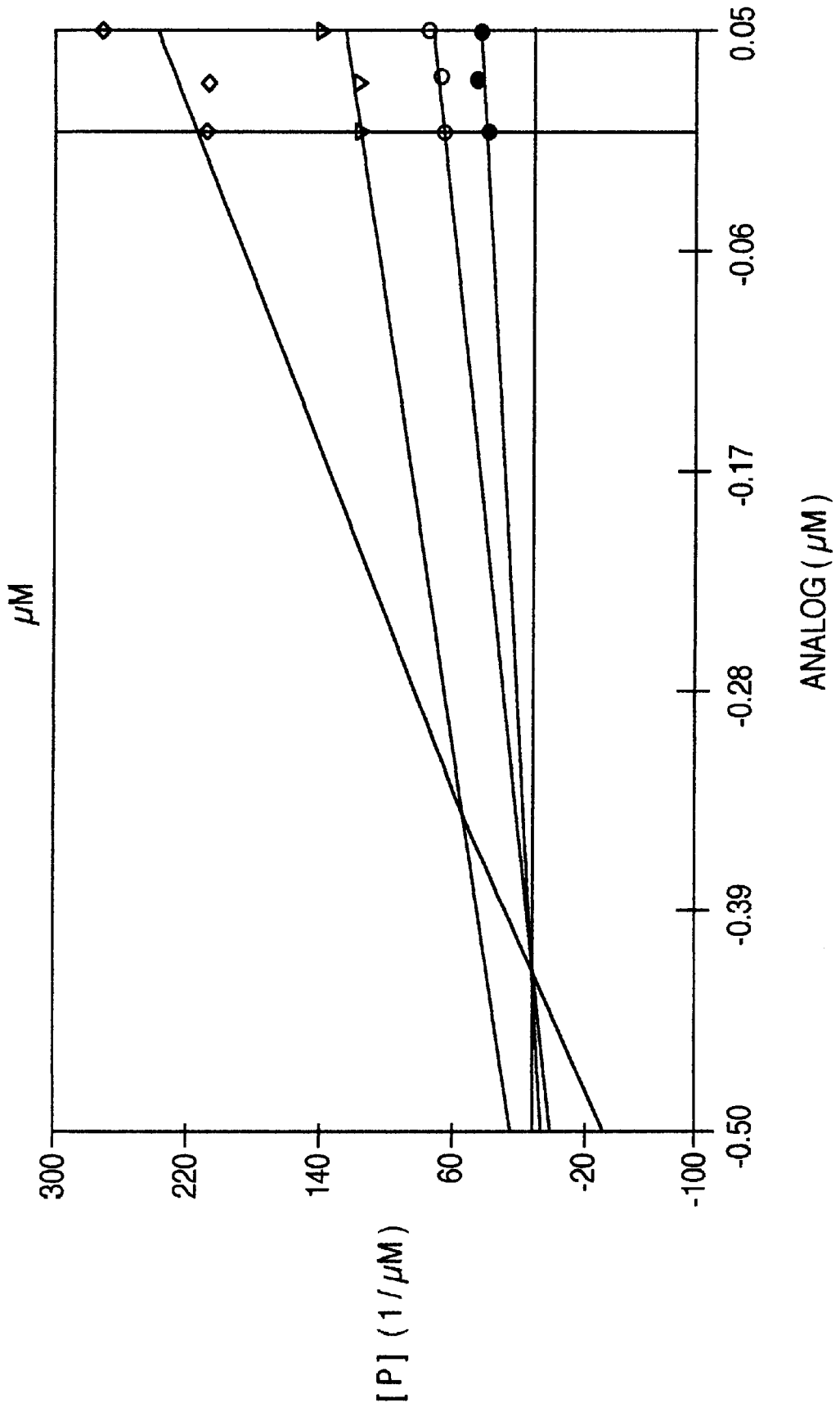
Figure 5A:
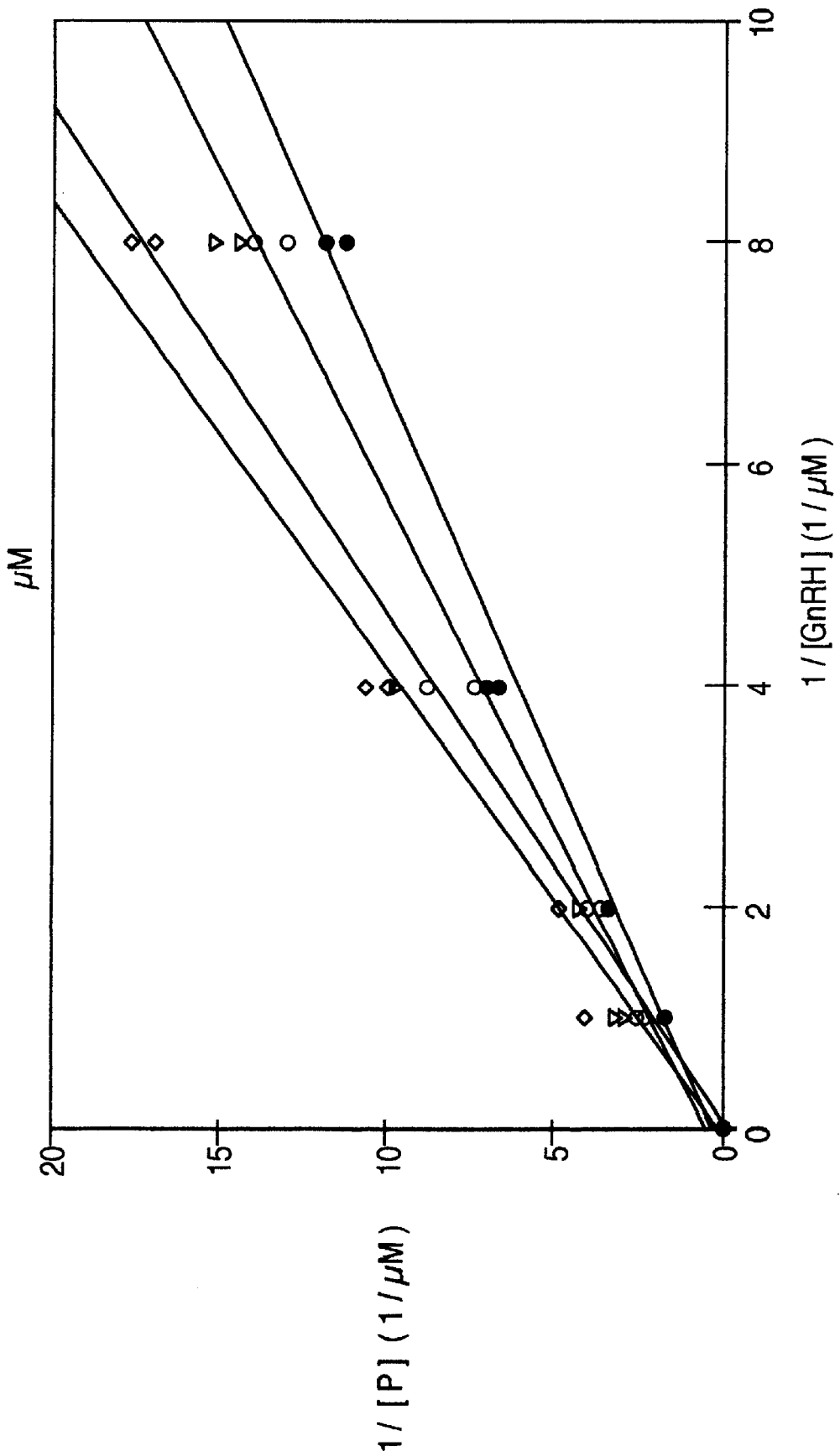
Figure 5B:
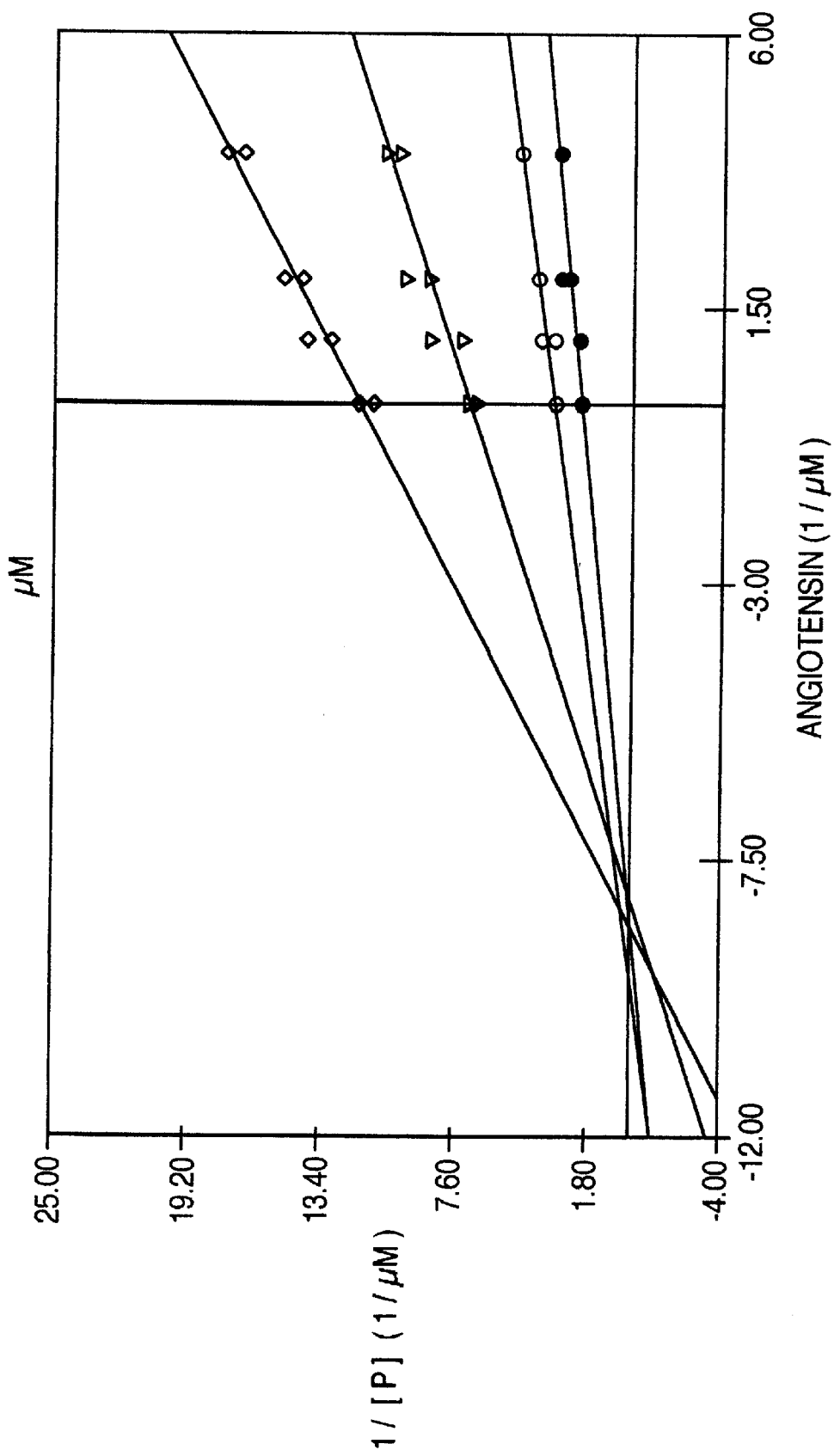
Figure 6:
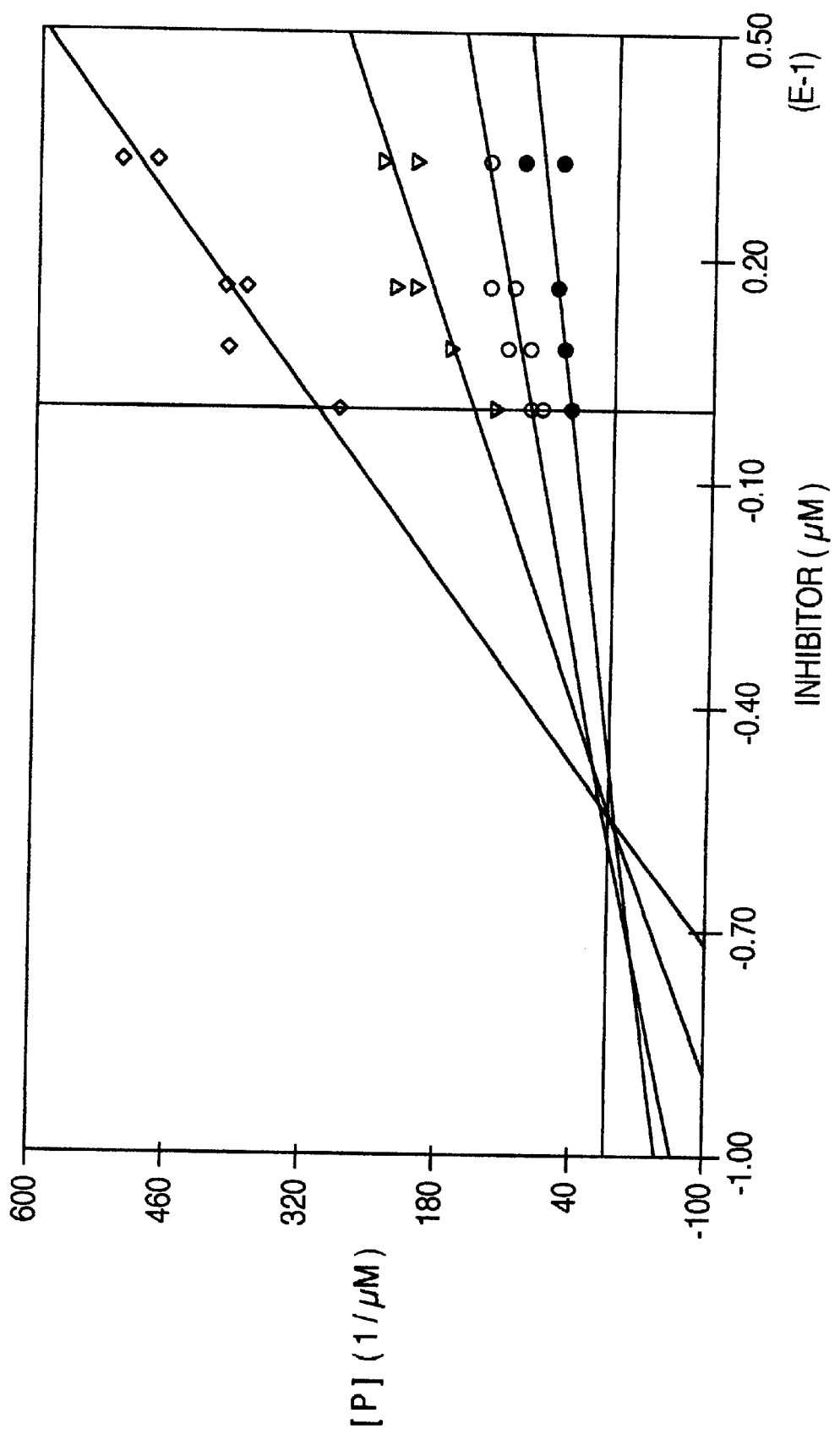
Figure 7:
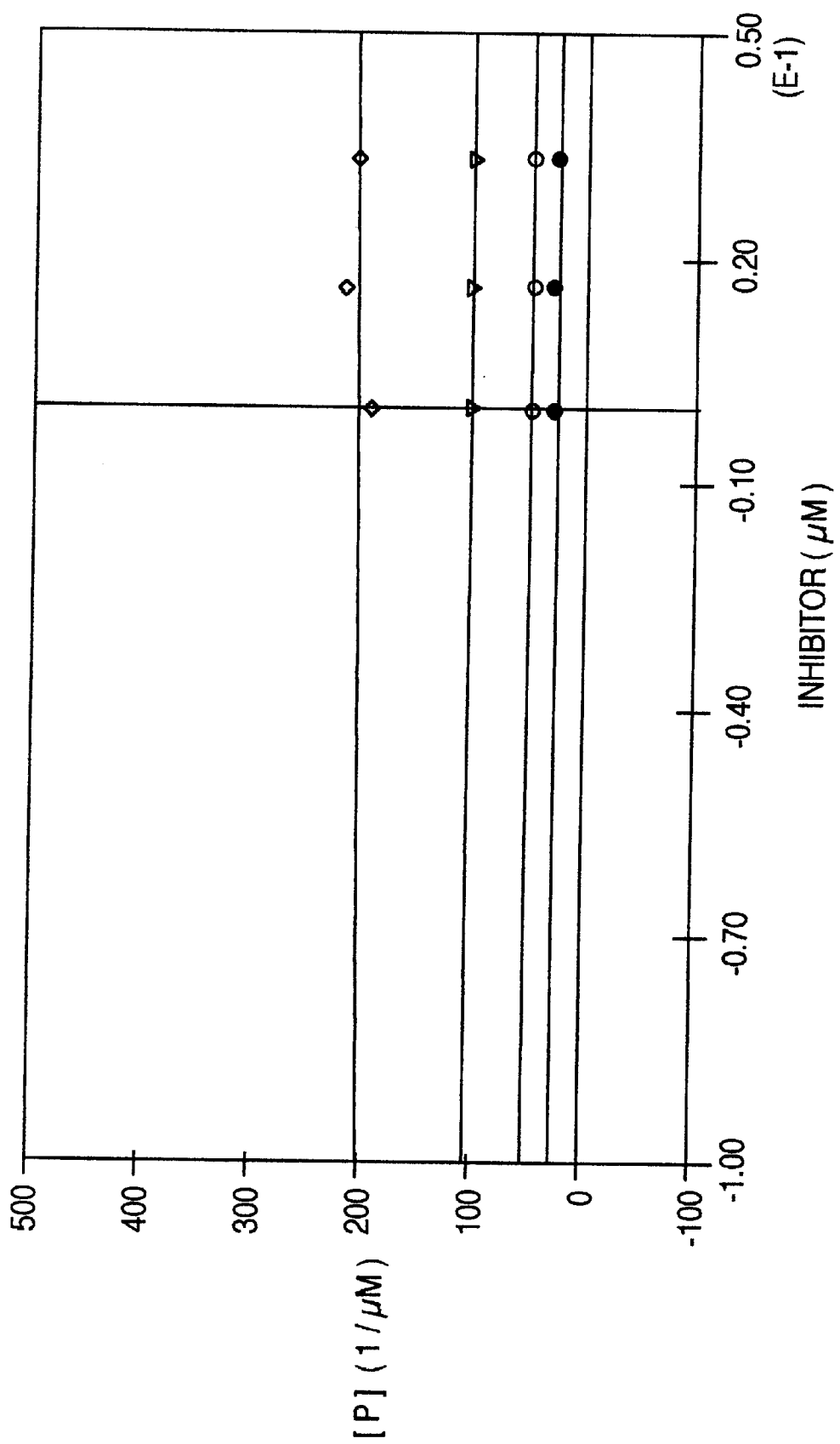

FIG. 4. Effect of Reduced Oxytocin on the Degradation of GnRH by C-ase-1.
GnRH 0.050 M, ○ GnRH 0.0250 M, ▽ GnRH 0.012 M, ◇ GnRH 0.062 M FIGS. 5A and 5B. Action of Angiotensin II on Degradation of GnRH. 5A
Angio 0.12 M, ○ Angio 0.25 M, ▽ Angio 0.50 M, ◇ Angio 1.000 M 5B
GnRH 1.00 M, β GnRH 0.50M, ▽ GnRH 0.25 M, ◇ GNRH 0.12 M FIG. 6. Effect of des-Gly$^{10}$-GnRH-ethylamide on Degradation of GnRH by C-ase-1.
GnRH 0.050 ○ GnRH 0.0250 M, ▽ GnRH 0.012 M, ◇ GnRH 0.062 M FIG. 7. Effect of des-Gly$^{10}$-Im-Btl-D-His$^6$-GnRH-ethylamide on Degradation of GnRH by C-ase-1.
GnRH0.0500 M, ○ GnRH0.0250M, ▽ GnRH0.012M, ◇ GnRH0.062 M

DETAILED DESCRIPTION OF THE PREFERRED EMBODIMENTS

Following long-standing patent law convention, the terms "a" and "an" mean "one or more" when used in this application, including the claims.

For purposes of describing the present invention the chorion is described as the highly vascularized outer embryonic membrane that is associated with the allantois in the formation of the placenta.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I
Design & Synthesis of Chorionic GnRH Analogs

The present example outlines how analogs of non-mammalian GnRH with increased activity in chorionic and ovarian tissues are synthesized.

Existing mammalian GnRH analogs are designed for activity at the pituitary GnRH receptor and with extended stability in the circulation of non-pregnant individuals. Yet, the existing data indicate that the chorionic GnRH receptor differs from that in the pituitary. In addition, the degradation of GnRH is different during pregnancy. Therefore, prior known pituitary mammalian GnRH analogs have not been designed for use during pregnancy, and potent non-mammalian GnRH analogs have not been designed for use during pregnancy. The present invention provides potent non-mammalian GnRH analogs.

Method and Analysis: Non-mammalian analogs of GnRH were synthesized. They were specifically designed to prevent degradation of the analog both in the maternal circulation as well as within the intrauterine tissues. This allows for the maintenance of sufficient concentrations of analog to remain active when administered via the maternal system and to reach the intrauterine tissue. Due to the particular specificity of the placental receptor and specific peptidase in maternal blood and placental tissue, the particular analogs of the invention were designed. Analogs of the Salmon and Chicken II GnRH sequences, that both show greater affinity for the placental receptor than for the pituitary receptor, were modified to the α-aza-Gly$^{10}$-NH$_2$ analog to make them resistant to degradation in the circulation and by C-ase-1 (chorionic GnRH analogs 1 and 2). The Chicken II GnRH sequence and the Salmon GnRH sequence were also modified at the 6 position using D-Arg, making it resistant to degradation by the endopeptidase in blood, and was modified at the 10 position making it stable in maternal blood and the chorionic tissues (chorionic GnRH analogs 2 and 4). These analogs are expected to have increased binding to the placental receptor and increased metabolic stability.

EXAMPLE II

Placental Receptor Binding Activity Placental Receptor Studies

The placental receptor binding activity of the different non-mammalian GnRH analogs of the present invention were compared. The human placental GnRH receptor is distinct from that at the pituitary. Prior mammalian GnRH analogs have been designed to increase activity at the pituitary GnRH receptor and stability in the circulation of non-pregnant individuals. These analogs do not demonstrate potent binding activity at the placental receptor as they do at the pituitary receptor. The non-mammalian GnRHs have been designed to interact with preference at the placental receptor and not the pituitary receptor. They have also been designed to limit degradation by the chorionic enzyme, C-ase-1, present in maternal circulation as well as the placenta. Placental binding activity of the newly synthesized chorionic GnRH analogs has been compared to that for existing pituitary-active analogs of mammalian GnRH.

Method and Analysis: The newly synthesized non-mammalian GnRH analogs and other commercially available analogs were used in placental receptors binding and enzyme stability studies described here. On the basis of these studies, the most receptor potent and most enzyme-stable analogs were chosen for further biopotency studies. GnRH receptors were purified from the membrane fractions from placentas. The purification procedure for the placental GnRH receptor was performed using a modification of the method described by Bramley et al., which reference is specifically incorporated herein by reference for the purpose. Bramley T A, McPhie C A, Menzies G S 1994 Human placental gonadotropin-releasing hormone (GnRH) binding sites: 111. Changes in GnRH binding levels with stage of gestation. Placenta 15:733–745. Addition of enzyme inhibitors for the endogenous C-ase-1 were used as well as agents for receptor stabilization. Initially, receptor-binding assays using $^{125}$I-Buserilin as label were performed. The competitive binding of each of the analogs was studied over a dose range of $10^{-11}$ to $10^{-6}$ M. Incubation was at room temperature and receptor bound label was precipitated with polyethyleneglycol. Specific and non-specific binding was determined. The data was subjected to Scatchard analysis. The non-mammalian analogs' ability to bind to the placental GnRH receptor was compared to that for synthetic mammalian GnRH, Buserilin and the newly synthesized non-mammalian GnRH analogs. The more potent analogs were then studied in homologous receptor assays using newly synthesized non-mammalian GnRH analog as the radioiodinated label. This way, the receptor affinity for that analog could be precisely determined. Receptors from three different term placentas were used to study each of these analogs. The most potent analogs were used for the C-ase-1 stability studies. These data enabled the inventor to predict the most potent non-mammalian GnRH analog structure for the placental GnRH receptor, and assisted in the design of even more potent analogs for the chorionic GnRH receptor.

EXAMPLE III

Placental Stability Studies

The present example demonstrated the utility of using the present invention in controlling and modulating the activity of the placenta, such as in a placenta of a pregnant mammal.

Mammalian GnRH and its analogs bind to placental receptors. The present non-mammalian analogs had not been examined for placental receptor binding. However, the added stability of these non-mammalian analogs, would effect a substantial increase in bioactivity alone. Thus, both stability and binding studies were performed.

Chorionic Peptidase-1 Stability Studies: The enzymatic degradation of the non-mammalian GnRH analogs were studied using the C-ase-1 enzyme activity assay as well as whole placental homogenate assays.

A chorionic peptidase that actively degrades GnRH in the placenta, named chorionic peptidase-1 (C-ase-1), was used. This enzyme acts as a post-proline peptidase, and is present in the placenta and in maternal circulation. In a non-pregnant individual very little post-proline peptidase activity is present in blood. Thus, currently available mammalian GnRH analogs have not been designed to be resistant to degradation by this activity. Non-mammalian GnRH analogs were designed with these specific criteria in mind. The stability of these non-mammalian GnRH analogs to the enzymatic activity of C-ase-1 and in placental homogenate was examined. In addition, the ability of the analogs to competitively inhibit the degradation of GnRH by C-ase-1 was studied.

Method and Analysis: The stability of most potent receptor-active non-mammalian GnRH analogs in the presence of C-ase-1 and placental homogenate was identified. Using the incubation system developed for the C-ase-1 activity, the degradation of each analog was tested. This method has previously been used by the investigator to determine the degradation of GnRH by C-ase-1 (100). Each of these analogs was then studied for their ability to act as a competitive inhibitor of non-mammalian GnRH for C-ase-1 activity. These studies were done using the C-ase-1 enzyme activity assay as described previously. In this assay, incubation of enzyme and mammalian GnRH with and without the chosen newly synthesized non-mammalian GnRH analog was studied. The reaction was stopped by heating, and the remaining mammalian GnRH substrate was quantified by radioimmunoassay. The product formed was calculated by subtraction, and its inverse plotted against the inverse of the original substrate concentrations to determine the nature of the competition. The $K_i$ was to be determined by plotting the inverse of the product that formed verses the inhibitor used.

Studies using whole placental homogenate were performed. The enzymatic degradation of mammalian GnRH was studied as described above, replacing C-ase-1 with placental homogenate. The competition by the newly synthesized non-mammalian GnRH analogs as compared to mammalian GnRH was then studied to confirm the C-ase-1 studies above. Similar patterns of inhibition using placental extracts demonstrated the dominance of the C-ase-1 activity in the degradation of GnRH during pregnancy.

Although the enzyme competition system had already been developed, newly synthesized non-mammalian GnRH analogs have not been utilized in these systems. Previous data generated by the present inventor has demonstrated that the antiserum is specific for mammalian GnRH, thus reducing potential for cross-reaction of non-mammalian GnRH or its analogs in the assay used in these studies.

EXAMPLE IV
Biological Activity Studies

The hCG inhibiting activity of the chorionic GnRH analogs was studied using an in vitro human placental explant system. The present example demonstrates the utility of using the present non-mammalian analogs to regulate hCG levels in a mammal and in the regulation of pregnancy.

The newly synthesized non-mammalian GnRH analogs are resistant to enzyme degradation and are potent binders of the placental GnRH receptor. Bio-potency was studied using a placental explant system, and by determining the release of hCG, progesterone and prostanoids. hCG is the luteotropin of pregnancy, and known to be critical to the maintenance of the corpus luteum during pregnancy. Thus, it is a primary parameter of interest. The production of progesterone by the placenta and the ovary is affected by hCG, as well as being independently regulated by a GnRH-like substance. Progesterone is primary to the maintenance of uterine quiescence and thus the maintenance of pregnancy, and therefore is of primary interest to these studies. Also, of interest is the effect of these GnRH analogs on prostaglandin production. Prostaglandins are required for abortifacient activity, and thus, the maintenance or increase in their production may be necessary for the proposed action of the analogs.

Method and analysis: The biological activity of the newly synthesized non-mammalian GnRH analogs was studied using a static implant culture system. This system allows for inexpensive extended activity studies. Mammalian GnRH action on the human placenta release of hCG, progesterone and prostaglandins were defined using this system. Siler-Khodr T M, Khodr G S, Valenzuela G, Rhode J 1986 Gonadotropin-releasing hormone effects on placental hormones during gestation: 1 Alpha-human chorionic gonadotropin, human chorionic gonadotropin and human chorionic somatomammotropin. Biol Reprod 34:245–254; Siler-Khodr T M, Khodr G S, Valenzuela G, Rhode J 1986 Gonadotropin-releasing hormone effects on placental hormones during gestation: II. Progesterone, estrone, estradiol and estriol. Biol Reprod 34:255–264; Siler-Khodr T M, Khodr G S, Valenzuela G, Harper J, Rhode J 1986 GnRH effects on placental hormones during gestation. 111 Prostaglandin E, prostaglandin F, and 13, 14-dihydro-15-keto-prostaglandin F. Biol Reprod 35:312–319. Replicate cultures were studied, thus allowing for comparison of different doses of each non-mammalian GnRH analog to mammalian GnRH, as well as direct competition assays. In these studies, the action of the most stable and receptor-active chorionic GnRH analogs on hCG, progesterone and prostaglandin $E_2$ were determined in the spent media using specific sensitive radioimmunoassays. These studies were repeated using different human placentas.

Using an in vitro system to define bio-potency is expected to be predictive of in vivo activity. In addition to placental action, these newly synthesized non-mammalian GnRH analogs are also expected to act directly at the corpus luteum to inhibit steroidogenesis. These analogs are also expected to be active at the ovarian level.

EXAMPLE V
Inhibition of Chorionic Peptidase-1 (C-ase-1) Activity by Analogues of GnRH The present example demonstrates the isolation of an enzyme from human placentas, and the action of the enzyme as a post-proline peptidase. It actively degrades peptides, such as gonadotropin releasing hormone (GnRH), thyrotrophin releasing hormone (TRH), oxytocin, and Angiotensin II (AGN-II). See FIGS. 3, 4, 5A, and 5B. These peptides contain a proline residue enzyme, chorionic peptidase-1 (C-ase-1).

The present example also defines enzyme inhibitors of C-ase-1 action on GnRH, such that it might regulate GnRH concentrations within the intrauterine tissues.

C-ase-1 enzyme activity studies were done by incubating GnRH with C-ase-1 in the presence of varying concentrations of the non-mammalian GnRH analogs. The reaction was stopped by heating at 85° C. for 10 minutes. The remaining GnRH was determined using a specific radioimmunoassay. The formation of product, i.e., the N-terminal nonapeptide of GnRH, was calculated by subtraction and its inverse was plotted versus the inverse of the initial substrate to determine the $K_5$ of the reaction. The inhibitory activity of Antide, $^6$Im-btl-D-His-GnRH-$^{10}$ ethylamide, $^9$OH-Pro-GnRH, Chicken II GnRH-$^{10}$ ethylamide, Chicken II GnRH, Chicken I GnRH, Salmon GnRH and Lamprey GnRH was studied. The relative potency of each analog was compared.

Figure 1:
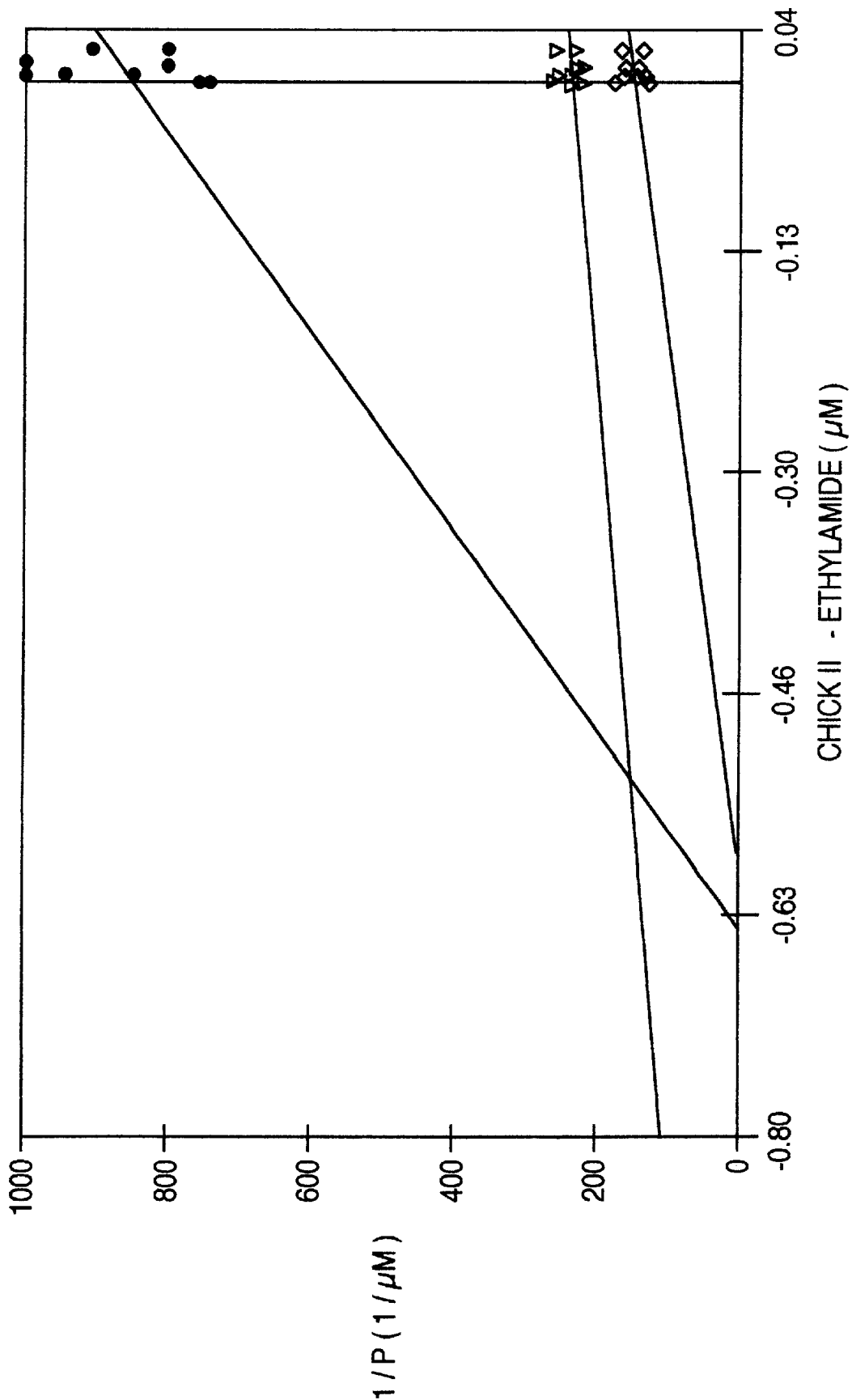
FIG. 1. Action of Chicken II-ethylamide On Degradation of GnRH By C-ase-1.
GnRH 0.00313 M, ▽ GnRH 0.0125 M, ◇ GnRH 0.0250M GnRH was actively degraded by C-ase-1. This activity of C-ase-1 was inhibited by, $^9$OH-Pro-GnRH, Lamprey, Chicken I-GnRH, Antide, Chicken II-GnRH and Salmon GnRH with a relative potency of 1.5, 1.5, 0.6, 0.6, and 0.2 and 0.2, respectively to that for GnRH. Both Chicken II GnRH-$^{10}$ ethylamide and $^6$I-btl-D-His-GnRH$^{10}$ ethylamide were essentially inactive, i.e., <0.001 inhibitory activity for GnRH.

GnRH was actively degraded by C-ase-1. This activity of C-ase-1 was inhibited by, $^9$OH-Pro-GnRH, Lamprey, Chicken I-GnRH, Antide, Chicken II-GnRH and Salmon GnRH with a relative potency of 1.5, 1.5, 0.6, 0.6, 0.2 and 0.2, respectively, compared to that for GnRH. Both Chicken II GnRH-$^{10}$ ethylamide and $^6$Im-btl-D-His-GnRH$^{10}$ ethylamide were essentially inactive, i.e., <0.001 inhibitory activity for GnRH. See FIG. 1.

Chorionic peptidase-1, which is a post-proline peptidase with high specificity for the degradation of GnRH, can also degrade other GnRH species. The synthetic mammalian GnRH analogs such as antide are degraded with reduced activity, while other analogs such as Chicken II GnRH-$^{10}$ ethylamide and $^6$Im-btl-D-His-GnRH$^{10}$ ethylamide are resistant to degradation by this endogenous chorionic enzyme. See FIG. 7. These analogs will be useful in the regulation of chorionicGnRH activity.

EXAMPLE VI
Comparison of GnRH and its Synthetic and Naturally Occurring Analogs for Binding Degradation Action in the Human Placental Receptor The human placental GnRH receptor shows different kinetic constants for GnRH compared to that of the pituitary receptor. The relative decreased potency of GnRH at the placental receptor, together with its rapid degradation in chorionic tissue, leads to question if it is indeed the active sequence for the chorionic receptor.

Studies were designed to compare the human placental receptor activity for numerous synthetic and naturally occurring analogs.

Receptor assays were performed by incubating human term placental GnRH receptors with varying concentrations of GnRH or its analogs in the presence of $^{125}$I-Buserilin. The reaction was stopped and the bound hormone precipitated with polyethylene glycol. Following centrifugation the receptor binding activity was calculated and compared for GnRH, $^6$Im-btl-D-His-GnRH-$^{10}$ ethylamide and $^6$D-Trp-GnRH-$^{10}$ ethylamide, Chicken II-GnRH and Chicken II GnRH-$^{10}$ ethylamide.

EXAMPLE VII
GnRH and Stability Thereof in the Presence of C-ase-1

Figure 2:
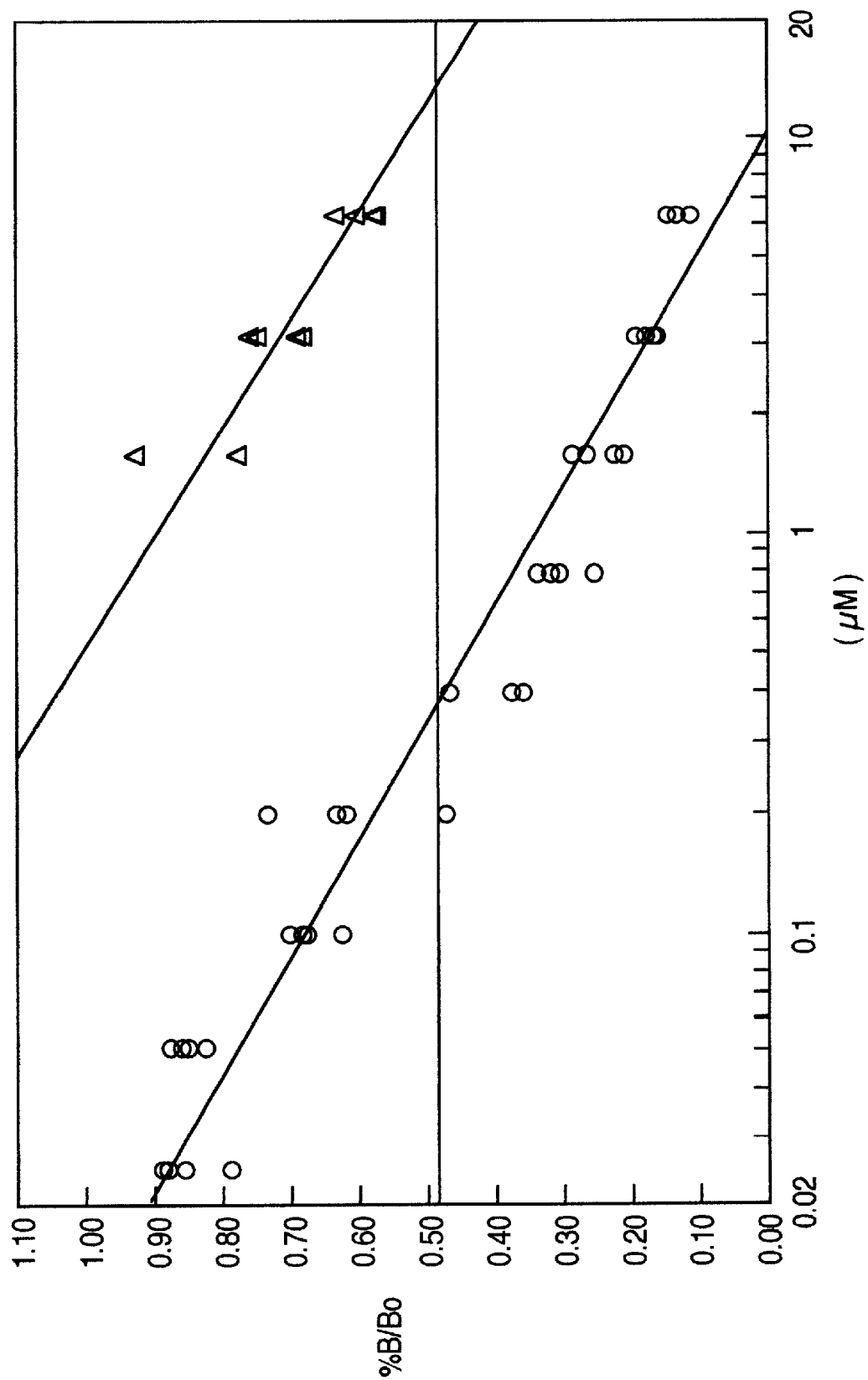
FIG. 2. Competitive Placental Receptor Binding For GnRH Analogs With Labeled Chicken II Analog.
Buserilin ▽ GnRH, ○ D-Arg-CII-EA GnRH was bound by the placental GnRH receptor with a $K_d$ of $10^{-6}$ M. Chicken II GnRH was similar to GnRH. The $K_d$ for $^6$Im-btl-D-His-GnRH-$^{10}$ ethylamide was half the potency of GnRH, while Buserilin and $^6$D-Trp-GnRH$^{-10}$ ethylamide were twice as active as GnRH. The greatest potency, having a $K_d$ of 3 non-mammalian, i.e. 33-fold more activity than GnRH.
Figure 3:
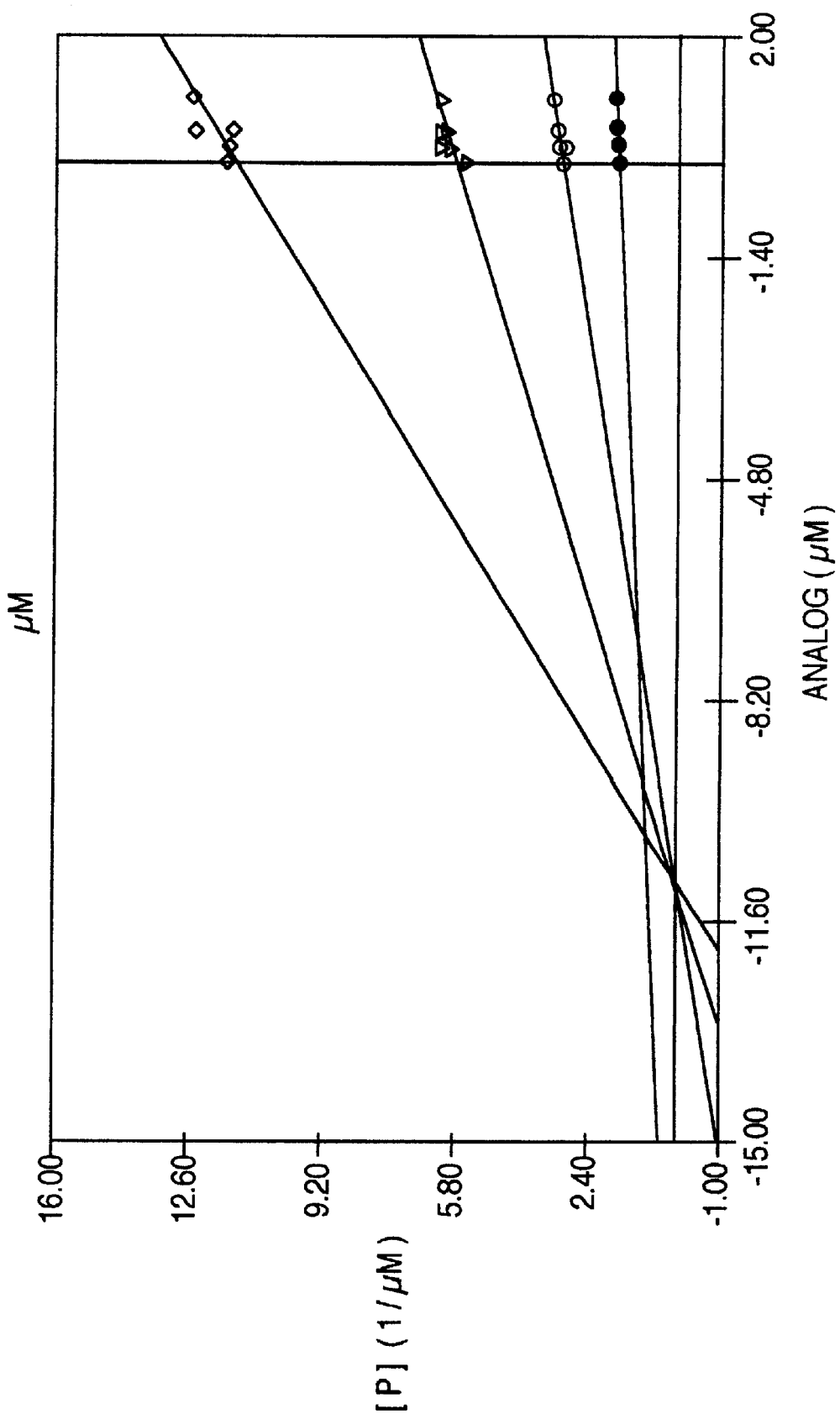
FIG. 3. Effect of TRH on the Degradation of GnRH by C-ase-1.

GnRH was bound by the placental GnRH receptor with a $K_d$ of $10^{-6}$M. Chicken II GnRH was similar to GnRH. The $K_d$ for -$^6$Im-btl-D-His-GnRH$^{10}$ ethylamide was half the potency of GnRH, while buserilin and $^6$D-Trp-GnRH-$^{10}$ ethylamide were twice as active as GnRH. The greatest potency, having a $K_d$ of 30 non-mammalian, i.e. 33-fold more activity than GnRH. See FIG. 2.

Fifteen GnRH analogs were examined for their stability in the presence of C-ase-1 and placental homogenate. Using the incubation system developed for the C-ase-1 activity, the degradation of each analog was studied. Previously, this method was used to determine the degradation of GnRH by C-ase-1. Each of these analogs was studied for their ability to act as competitive inhibitors of GnRH for C-ase-1 activity (Table 1). The inverse of the product was plotted against the inverse of the original substrate concentrations to determine $K_s$ of the competition. The $K_i$ was determined by plotting the inverse of the product formed verses the inhibitor used. The placental homogenate studied demonstrated a similar pattern having $K_i$ three-fold greater than that for C-ase-1.

OH-Pro(9)-GnRH and Lamprey GnRH were determined to be better competitors for GNRH degradation by C-ase-1. They are as or even more potent than GnRH. Antide and Chicken I GnRH are three-fold less potent than GnRH, but two-fold more potent than the Salmon or Chicken II GnRHs defined here. The addition of the ethylamide to GnRH, with or without the D-Trp(6)-, D-Phe(6) substitution, decreased the competition with GnRH for C-ase-1 degradation, but not as markedly as did the Im-btl-D-His(6) or Chicken II GnRH-ethylamides. Ethylamides of the latter two GnRHs were greater than 200-fold less active in the inhibition of GnRH degradation by C-ase-1. Thus, these ethylamides appear to be very stable in the presence of the C-ase-1 enzyme. The Im-btl-D-His(6) analog has reduced receptor potency. The stability of the D-Arg-(6)-Chicken II GnRHaza-Gly-amide was found to be at least 200-fold that of GnRH.

The stability of these analogs in the present of whole placental homogenates was examined. The ethylamide derivative has a slowed degradation rate as compared to GnRH, but can be degraded. Chicken II and its ethylamide analog are more stable than the mammalian GnRH analogs analyzed to date.

TABLE 1

Inhibitor Constants For Analogs Of GnRH

| Analog of GnRH | $K_{i\text{-for C-ase-1(non-mammalian)}}$ |
|---|---|
| Mammalian | 30 |
| Lamprey | 20 |
| Salmon | 300 |
| Chicken I | 80 |
| Chicken II | 200 |
| Chicken II EA (10) | 130 |
| Chicken II D-Arg (6), aza-Gly (10) amide | >200 |
| Salmon II D-Arg (6), aza-Gly (10) amide | 200 |
| Mammalian D-Trp (6) | 20 |
| Mammalian EA (10) | 70 |
| Mammalian D-Trp (6), EA (10) | 60 |
| Mammalian D-Leu (6), EA (10) | 80 |
| Mammalian But-D-Ser (6), EA (10) | 110 |
| Mammalian Im-btl-D-His (6), EA (10) | >200 |
| Antide | 120 |

Bio-potency Data

The hCG inhibiting activity of the GnRH analogs was studied using an in vitro human placental explant system. The newly synthesized GnRH analogs are resistant to enzyme degradation and one potent binders of the placental receptor. The bio-potency was done with a placental explant system, and the release of hCG, progesterone and prostaglandin $E_2$ was assessed. hCG is the luteotropin of pregnancy and known to be important in the maintenance of the corpus luteum during pregnancy. The production of progesterone by the placenta is affected by hCG, and may be independently regulated by GnRH as well. Progesterone is primary to the maintenance of uterine quiescence and thus the maintenance of pregnancy. Of interest was the effect of these GnRH analogs on prostaglandin production. Prostaglandins are required for abortifacient activity.

These studies were done using the D-Arg(6)-Chicken II GnRH-aza-Gly(10)-amide analog. Three different placentas have been used for these studies and the data analysis of one of these placental culture sets is attached.

An inhibition of hCG was observed with this analog regardless of the concentration of exogenous GnRH. The lower dose of analog was the most effective in this particular study. Progesterone response to this analog was similar to hCG.

These data demonstrate the complexity of a system having multiple types of GnRH receptors. D-Arg(6)-Chicken II GnRH analog-$NH_2$ has bioactivity in the regulation of hCG and progesterone in the human term placenta.

These studies demonstrate specific binding of GnRH analogs to the human GnRH placental receptor, which is unique from the pituitary receptor. The most potent analogs were Chicken II GnRH derivatives, particularly the D-Arg (6)-Chicken II GnRH-aza-Gly$^{10}NH_2$. This analog may be used in the regulation of chorionic GnRH activity.

EXAMPLE VIII

Non-Mammalian GNRH and Methods for Maintaining Pregnancy

The present example defines a method by which the present invention may be used to maintain pregnancy in a pregnant mammal. The mammal in some embodiments is a pregnant human. As a proposed dose regimen, it is anticipated that a pregnant female between 100 lbs and 150 lbs would be administered about 10 nanogram to 1.0 gram of Chicken II GnRH Analog or Salmon GnRH analog. This would be expected to be effective for promoting the maintenance of pregnancy in the mammal when administered.

In some embodiments, the dosing regimen will comprise a pulsatile administration of the Chicken II GnRH over a 24-hour period, wherein the daily dosage is administered in relatively equal $\frac{1}{24}^{th}$ fractions. For example, where the daily dose is about 2.4 micrograms, the patient would be administered about 0.1 micrograms per hour over a 24-hour period. Such a daily pulsatile administration would create a hormonal environment in the patient sufficient to maintain pregnancy. The particular pharmaceutical preparations may be created by one of skill in the pharmaceutical arts. Remington's Pharmaceutical Sciences Remington: The Science and Practice of Pharmacy, $19^{th}$ edition, Vol. 102, A. R. Gennaro, ed., Mack Publishing co. Easton, Pa. (1995), is specifically incorporated herein by reference for this purpose.

EXAMPLE IX

Non-Mammalian GNRH Analogs and Post Coital Contraception, Menses-Inducement

The present example demonstrates the utility of the present invention for use as a post-coital contraceptive preparation.

By way of example, the analogs defined here, and conservative variants thereof, may be formulated into a pharmaceutically acceptable preparation, and then administered to a female mammal having been inseminated during the prior 24 to 72 hours (prior 1 to 3 days). Relatively high doses of about 0.1 gram to about 10 grams of the non-mammalian GnRH analog would be given daily for 2 to 5 days, on the average about 3 days.

To induce menses, it is anticipated that a dose of between 0.1 grams micrograms to 10.0 grams for 3 days would be adequate to commence menses in the female mammal.

For purposes of practicing the present invention as an oligonucleotide in molecular biology applications, the non-mammalian GnRH analogs of Chicken II and Salmon decapeptide GnRH analog cDNA sequences would be employed. The textbook of Sambrook, et al (1989) *Molecular Cloning, A Laboratory Manual,* 2d Ed., Cold Springs Harbor Laboratory, Cold Springs Harbor, N.Y., is specifically incorporated herein by reference for this purpose. By way of example, the cDNA sequence for the non-mammalian GnRH of SEQ ID NO: 1 (Chicken II GnRH) or SEQ ID NO:3, (Salmon GnRH) may be prepared as part of a suitable vector, such as in an adenovirus or retroviral vector, and administered to the animal. Once the sequence is incorporated into the cell, the peptide product will be translated and peptide supplied. Because this method of treatment would not require that the peptide travel in the blood circulation in order to reach the site of action, there would be no requirement that the analog possess enzyme degradation resistance. This mode of treatment has not thus far been proposed, and hence the use of such a method in the regulation of female fertility is a novel clinical regimen.

The non-mammalian analogs are also contemplated to be useful to directly affect the ovary. By way of example, this technique renders the system useful as a contraceptive. As a contraceptive, the non-mammalian GnRH analog would be given daily from the start of ovulation and continue 8 days to two weeks, stopping with onset of menses.

EXAMPLE X

Antibodies Specific for Non-Mammalian GNRH

The present example demonstrates the utility for using the present invention non-mammalian GnRH analog decapeptides to prepare antibodies that preferentially bind the GnRH peptide sequences, or that bind the ovarian, placental or any other non-pituitary GnRH peptide or protein. It is anticipated that these non-mammalian GnRH analog antibodies may be used in a variety of screening assays. For example, these antibodies may be used to determine levels of GnRH present in a sample as an indicator molecule. The levels of such GnRH may be used to monitor and follow a patient's pregnancy, as well as an indicator of the length of gestation. The antibodies to non-mammalian GnRH may be monoclonal or polyclonal antibodies.

Polyclonal antibodies may be created by standard immunization techniques, wherein the immunogen used will be the non-mammalian Chicken-II GnRH analog or the Salmon GnRH analog decapeptide described herein. These peptides may be used either alone or together in a pharmaceutically acceptable adjuvant. The animal, such as a rabbit, would be administered several doses of the decapeptide preparation, and the levels of the animal's antibody blood levels monitored until an acceptable antibody level (titer) had been reached.

For the preparation of monoclonal antibodies, one would follow standard techniques for the immunization of an animal, again using the decapeptide non-mammalian GnRH peptide. Once sufficiently high acceptable antibodies are reached (titer) in the animal, the spleen of the animal would be harvested, and then fused with an immortalized cell line, such as a cancer cell line, to produce a population of hybridoma cells. This hybridoma population of cells would then be screened for those that produce the highest amount of antibody that specifically bind the non-mammalian GnRH analog decapeptide. Such hybridoma cells would be selected, and then cultured. The antibody to non-mammalian GnRH would then be collected from the media of the cell culture using techniques well know to those of skill in the art.

For purposes of the practice of preparing polyclonal and monoclonal antibody, the textbook Sambrook et al (1989) *Molecular Cloning, A Laboratory Manual,* $2^{nd}$ Ed., Cold Springs Harbor Laboratory, Cold Springs Harbor, N.Y., is specifically incorporated herein by reference. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents, which are both chemically and physiologically related, might be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A Chicken II GnRH decapeptide analog, having the sequence p-Glu-His-Trp-Ser-His-Xaa1-Trp-Tyr-Pro-Xaa2, capable of binding to human chorionic, placental or ovarian GnRH receptors and active in the presence of a post-proline peptidase or an endopeptidase, said analog comprising a D-amino acid substitution at position 6 and an ethylamide or aza-Gly-amide substitution at position 10.

2. The Chicken II GnRH decapeptide analog of claim 1 wherein the Chicken II GnRH analog is further defined as:

D-Arg(6)-Chicken II GnRH-ethylamide; or

D-Arg(6)-Chicken II GnRH-aza-Gly(10)-amide.

3. The Chicken II GnRH decapeptide analog of claim 2 wherein the Chicken II GnRH analog is further defined as D-Arg(6)-Chicken II GnRH-aza-Gly(10)-amide having a sequence as defined in SEQ ID NO: 2 (p-Glu-His-Trp-Ser-His-D-Arg-Trp-Tyr-Pro-$\alpha$-aza-Gly-$NH_2$).

4. The Chicken II GnRH decapeptide analog of claim 3 wherein the Chicken II GnRH analog has a cDNA sequence of SEQ ID NO.1: (CAG CAC TGG TCT CAT GGC TGG TAT CCT GGA).

5. A pharmaceutical preparation comprising a compound according to claim 3, in admixture with a pharmaceutically acceptable carrier, diluent or excipient.

6. The Chicken II GnRH decapeptide analog of claim 1 wherein the post-proline peptidase is chorionic peptidase-1.

7. The Chicken II GnRH decapeptide analog of claim 1 wherein the Chicken II GnRH analog is further defined as an aza-Gly(10)-amide GnRH analog.

8. The Chicken II GnRH decapeptide analog of claim 1 wherein the Chicken II GnRH analog is further defined as comprising a D-Arg, a D-Leu, D-tBu-serine, or a D-Trp substitution at position 6 and an aza-Gly amide or an ethylamide at position 10.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Chicken II GnRH

<400> SEQUENCE: 1
cagcactggt ctcatggctg gtatcctgga                                       30

<210> SEQ ID NO 2
<211> LENGTH: 10
<212> TYPE: Prt
<213> ORGANISM: Chicken II GnRH
<220> FEATURE:
<221> NAME/KEY: mat_peptide
<222> LOCATION: Within brain mRNA 121-150, within brain gene 2174-2203.
```

```
<223> OTHER INFORMATION: MOD_RES substitution of Gly residue at 10
      by -aza-Gly-NH2. Xaa represents D-Arg.MOD_RES Glu at position 1
      is pyroglutamic acid.

<400> SEQUENCE: 2

Glu His Trp Ser His Xaa Trp Tyr Pro Gly
                5                   10

<210> SEQ ID NO 3
<211> LENGTH: 30
<212> TYPE: DNA
<213> ORGANISM: Salmon GnRH

<400> SEQUENCE: 3
cagcactggt cttatggctg gctgcctgga                                    30

<210> SEQ ID NO 4
<211> LENGTH: 10
<212> TYPE: Prt
<213> ORGANISM: Salmon GnRH
<220> FEATURE:
<221> NAME/KEY: mat_peptide
<222> LOCATION: unknown
<223> OTHER INFORMATION: MOD_RES substitution of Gly residue at
      10 with -aza-Gly-NH2. Xaa represents D-Arg.MOD_RES Glu at
      position 1 is pyroglutamic acid.

<400> SEQUENCE: 4

Glu His Trp Ser Tyr Xaa Trp Leu Pro Gly
                5                   10
```